United States Patent
Sumita

(10) Patent No.: US 7,090,753 B2
(45) Date of Patent: Aug. 15, 2006

(54) ELECTROLYTIC CELL FOR PRODUCING CHARGED ANODE WATER SUITABLE FOR SURFACE CLEANING OR TREATMENT, AND METHOD FOR PRODUCING THE SAME AND USE OF THE SAME

(75) Inventor: Osao Sumita, Tokyo (JP)

(73) Assignee: Oculus Innovative Sciences, Inc., Petaluma, CA (US)

( * ) Notice: Subject to any disclaimer, the term of this patent is extended or adjusted under 35 U.S.C. 154(b) by 301 days.

(21) Appl. No.: 10/242,779

(22) Filed: Sep. 13, 2002

(65) Prior Publication Data

US 2003/0056805 A1  Mar. 27, 2003

(30) Foreign Application Priority Data

Sep. 14, 2001 (JP) ............................. 2001-279624

(51) Int. Cl.
*C25B 9/12* (2006.01)
*C25B 1/00* (2006.01)
*C02F 1/461* (2006.01)

(52) U.S. Cl. ................. 204/263; 204/252; 204/225
(58) Field of Classification Search ............ None
See application file for complete search history.

(56) References Cited

U.S. PATENT DOCUMENTS

| | | | |
|---|---|---|---|
| 3,066,095 A | 11/1962 | Hronas | |
| 3,975,246 A | 8/1976 | Eibl et al. | |
| 4,048,032 A | 9/1977 | Eibl | |
| 4,121,991 A | 10/1978 | Miller et al. | |
| 4,236,992 A | 12/1980 | Themy | |
| 4,242,446 A | 12/1980 | Madappally et al. | |
| 4,289,599 A * | 9/1981 | Fushihara | 204/240 |
| 4,296,103 A | 10/1981 | Laso | |
| 4,767,511 A | 8/1988 | Aragon | |
| 4,979,938 A | 12/1990 | Stephen et al. | |
| 5,079,010 A | 1/1992 | Natterer et al. | |
| 5,084,011 A | 1/1992 | Grady | |
| 5,244,768 A | 9/1993 | Inaba | |

(Continued)

FOREIGN PATENT DOCUMENTS

CN  1 231 994 A  10/1999

(Continued)

OTHER PUBLICATIONS

European Search Report for EP 1 103 264.

(Continued)

*Primary Examiner*—Harry D. Wilkins, III
(74) *Attorney, Agent, or Firm*—Leydig, Voit & Mayer, Ltd.

(57) ABSTRACT

The present invention provides an electrolytic cell, which can efficiently produce, charged water having an excellent performance of improving surface cleaning or treatment of an object, e.g., semiconductor, glass, or resin and of cleaning and sterilizing medical device.

The electrolytic cell of the present invention is for producing charged anode water suitable for surface cleaning or treatment, including the cathode chamber 41 and anode chamber 50, fluorinated cation-exchange membrane 46 provided to separated these chambers from each other, cathode 44 closely attaché to the cation-exchange membrane 45 on the side facing the cathode chamber 41, and middle chamber 48 filled with the cation-exchange resin 46, provided on the other side of The cation-exchange membrane 46, the cation-exchange resin 46 being arranged in such a way to come into contact with the fluorinated cation-exchange membrane 45, wherein the feed water is passed into the middle chamber 48 and passed thorough The anode chamber 50 to be recovered as the charged anode water.

20 Claims, 14 Drawing Sheets

U.S. PATENT DOCUMENTS

| | | | |
|---|---|---|---|
| 5,271,943 A | 12/1993 | Bogart et al. | |
| 5,334,383 A | 8/1994 | Morrow | |
| 5,376,242 A | 12/1994 | Hayakawa | |
| 5,427,667 A | 6/1995 | Bakhir et al. | |
| 5,445,722 A | 8/1995 | Yamaguti et al. | |
| 5,474,662 A | 12/1995 | Miyamae | |
| 5,507,932 A | 4/1996 | Robinson | |
| 5,510,009 A | 4/1996 | Arai et al. | |
| 5,543,030 A | 8/1996 | Shiramizu et al. | |
| 5,560,816 A | 10/1996 | Robinson | |
| 5,578,022 A | 11/1996 | Scherson et al. | |
| 5,593,554 A * | 1/1997 | Yamanaka et al. | 204/252 |
| 5,599,438 A | 2/1997 | Shiramizu et al. | |
| 5,615,764 A | 4/1997 | Satoh | |
| 5,616,221 A | 4/1997 | Aoki et al. | |
| 5,620,587 A | 4/1997 | Nakamura | |
| 5,622,725 A | 4/1997 | Kross | |
| 5,622,848 A | 4/1997 | Morrow | |
| 5,624,535 A | 4/1997 | Tsuchikawa et al. | |
| 5,628,848 A | 5/1997 | Friese et al. | |
| 5,635,040 A | 6/1997 | Bakhir et al. | |
| 5,635,053 A | 6/1997 | Aoki et al. | |
| 5,662,625 A | 9/1997 | Westwood | |
| 5,674,365 A | 10/1997 | Sano | |
| 5,674,537 A | 10/1997 | Morrow | |
| 5,720,869 A | 2/1998 | Yamanaka et al. | |
| 5,728,274 A | 3/1998 | Kamitani et al. | |
| 5,728,287 A | 3/1998 | Hough et al. | |
| 5,731,008 A | 3/1998 | Morrow | |
| 5,736,027 A | 4/1998 | Nakamura | |
| 5,759,478 A | 6/1998 | Kajiwara et al. | |
| 5,762,779 A | 6/1998 | Shiramizu et al. | |
| 5,783,052 A | 7/1998 | Bakhir et al. | |
| 5,792,090 A | 8/1998 | Ladin | |
| 5,798,028 A | 8/1998 | Tsuchikawa et al. | |
| 5,833,831 A | 11/1998 | Kitajima et al. | |
| 5,843,291 A | 12/1998 | Eki et al. | |
| 5,858,201 A | 1/1999 | Otsuka et al. | |
| 5,858,202 A | 1/1999 | Nakamura | |
| 5,871,623 A | 2/1999 | Bakhir et al. | |
| 5,888,357 A | 3/1999 | Mitsumori et al. | |
| 5,897,757 A | 4/1999 | Sano | |
| 5,900,257 A | 5/1999 | Breton et al. | |
| 5,902,619 A | 5/1999 | Rubow et al. | |
| 5,906,810 A | 5/1999 | Turner | |
| 5,928,488 A | 7/1999 | Newman | |
| 5,928,491 A | 7/1999 | Yu et al. | |
| 5,932,171 A | 8/1999 | Malchesky | |
| 5,938,915 A | 8/1999 | Morisawa | |
| 5,938,916 A | 8/1999 | Bryson et al. | |
| 5,944,978 A | 8/1999 | Okazaki | |
| 5,948,220 A | 9/1999 | Kamitani et al. | |
| 5,951,859 A | 9/1999 | Miura et al. | |
| 5,963,435 A | 10/1999 | Biernson | |
| 5,964,089 A | 10/1999 | Murphy et al. | |
| 5,965,009 A | 10/1999 | Shimamune et al. | |
| 5,980,703 A * | 11/1999 | Yamada et al. | 204/253 |
| 5,985,110 A | 11/1999 | Bakhir et al. | |
| 5,993,639 A | 11/1999 | Miyashita et al. | |
| 5,997,717 A | 12/1999 | Miyashita et al. | |
| 6,007,686 A | 12/1999 | Welch et al. | |
| 6,007,693 A | 12/1999 | Silveri | |
| 6,007,696 A | 12/1999 | Takayasu et al. | |
| 6,033,539 A | 3/2000 | Gablenko | |
| 6,056,866 A | 5/2000 | Maeda et al. | |
| 6,059,941 A | 5/2000 | Bryson et al. | |
| 6,093,292 A | 7/2000 | Akiyama | |
| 6,106,691 A | 8/2000 | Nakamura et al. | |
| 6,117,285 A | 9/2000 | Welch et al. | |
| 6,121,317 A | 9/2000 | Wu et al. | |
| 6,126,796 A | 10/2000 | Shimamune et al. | |
| 6,126,810 A | 10/2000 | Fricker et al. | |
| 6,139,876 A | 10/2000 | Kolta | |
| 6,143,163 A * | 11/2000 | Sawamoto et al. | 205/742 |
| 6,149,780 A | 11/2000 | Miyake | |
| 6,171,551 B1 | 1/2001 | Malchesky et al. | |
| 6,174,419 B1 | 1/2001 | Akiyama | |
| 6,187,154 B1 | 2/2001 | Yamaguchi et al. | |
| 6,200,434 B1 | 3/2001 | Shinjo et al. | |
| 6,210,748 B1 | 4/2001 | Nagahara et al. | |
| 6,228,251 B1 | 5/2001 | Okazaki | |
| 6,231,747 B1 | 5/2001 | Fukuzuka et al. | |
| 6,231,878 B1 | 5/2001 | Komatu et al. | |
| 6,251,259 B1 | 6/2001 | Satoh et al. | |
| 6,258,225 B1 | 7/2001 | Yamaoka | |
| 6,277,266 B1 | 8/2001 | Yamaoka | |
| 6,280,594 B1 | 8/2001 | Yamaoka | |
| 6,294,073 B1 * | 9/2001 | Shirota et al. | 205/749 |
| 6,296,744 B1 | 10/2001 | Djeiranishvili et al. | |
| 6,333,054 B1 | 12/2001 | Rogozinski | |
| 6,342,150 B1 | 1/2002 | Sale et al. | |
| 6,350,376 B1 | 2/2002 | Imaoka et al. | |
| 6,358,395 B1 | 3/2002 | Schorzman et al. | |
| 6,361,665 B1 | 3/2002 | Vorack | |
| 6,368,592 B1 | 4/2002 | Colton et al. | |
| 6,375,809 B1 | 4/2002 | Kato et al. | |
| 6,384,363 B1 | 5/2002 | Hayakawa et al. | |
| 6,391,169 B1 | 5/2002 | Hara et al. | |
| 6,426,066 B1 | 7/2002 | Najafi et al. | |
| 6,444,255 B1 | 9/2002 | Nagahara et al. | |
| 6,462,250 B1 | 10/2002 | Kuriyama et al. | |
| 6,464,845 B1 | 10/2002 | Shirota et al. | |
| 6,475,371 B1 | 11/2002 | Shirahata et al. | |
| 6,506,416 B1 | 1/2003 | Oakauchi et al. | |
| 6,527,940 B1 | 3/2003 | Shimamune et al. | |
| 6,544,502 B1 | 4/2003 | Heesch | |
| 6,551,492 B1 | 4/2003 | Hanaoka | |
| 6,565,736 B1 | 5/2003 | Park et al. | |
| 6,585,867 B1 | 7/2003 | Asano | |
| 6,585,868 B1 | 7/2003 | Chihara | |
| 6,620,315 B1 | 9/2003 | Martin | |
| 6,623,615 B1 | 9/2003 | Morisawa et al. | |
| 6,623,695 B1 | 9/2003 | Malchesky et al. | |
| 6,632,347 B1 | 10/2003 | Buckley et al. | |
| 6,638,364 B1 | 10/2003 | Harkins et al. | |
| 6,638,413 B1 | 10/2003 | Weinberg et al. | |
| 6,716,335 B1 | 4/2004 | Takesako et al. | |
| 6,723,226 B1 | 4/2004 | Takayasu et al. | |
| 6,743,351 B1 | 6/2004 | Arai et al. | |
| 6,752,757 B1 | 6/2004 | Muir et al. | |
| 6,815,551 B1 | 11/2004 | Albiez et al. | |
| 6,823,609 B1 | 11/2004 | Moretti | |
| 6,827,849 B1 | 12/2004 | Kurokawa et al. | |
| 6,833,206 B1 | 12/2004 | Erdle et al. | |
| 6,833,207 B1 | 12/2004 | Joos et al. | |
| 6,838,210 B1 | 1/2005 | Sawa | |
| 6,843,448 B1 | 1/2005 | Parmley | |
| 6,844,026 B1 | 1/2005 | Anthony et al. | |
| 6,852,205 B1 | 2/2005 | Toyoshima et al. | |
| 6,855,233 B1 | 2/2005 | Sawada | |
| 6,855,490 B1 | 2/2005 | Sompuram et al. | |
| 6,856,916 B1 | 2/2005 | Shyu | |
| 6,866,756 B1 | 3/2005 | Klein | |
| 6,867,048 B1 | 3/2005 | Kovacs | |
| 6,874,675 B1 | 4/2005 | Kida et al. | |
| 6,887,601 B1 | 5/2005 | Moulthrop et al. | |
| 6,921,743 B1 | 7/2005 | Scheder et al. | |
| 6,923,893 B1 | 8/2005 | Sano | |
| 2001/0012544 A1 | 8/2001 | Nagahara et al. | |
| 2001/0022273 A1 | 9/2001 | Popov et al. | |
| 2002/0023847 A1 | 2/2002 | Natsume | |
| 2002/0027070 A1 | 3/2002 | Oyokota et al. | |
| 2002/0027079 A1 | 3/2002 | Hanaoka | |
| 2002/0027084 A1 | 3/2002 | Park et al. | |

| | | |
|---|---|---|
| 2002/0032141 A1 | 3/2002 | Harkins |
| 2002/0036134 A1 | 3/2002 | Shirota et al. |
| 2002/0074237 A1 | 6/2002 | Takesako et al. |
| 2002/0112314 A1 | 8/2002 | Harkins |
| 2002/0134691 A1 | 9/2002 | Satoh et al. |
| 2002/0135220 A1 | 9/2002 | Yamaguchi et al. |
| 2002/0160053 A1 | 10/2002 | Yahagi et al. |
| 2002/0165220 A1 | 11/2002 | Heesch |
| 2002/0165431 A1 | 11/2002 | Muir et al. |
| 2002/0168418 A1 | 11/2002 | Lorenz et al. |
| 2002/0175085 A1 | 11/2002 | Harkins et al. |
| 2002/0176885 A1 | 11/2002 | Najafi et al. |
| 2002/0179884 A1 | 12/2002 | Hoshino et al. |
| 2002/0182262 A1 | 12/2002 | Selkon |
| 2003/0015418 A1 | 1/2003 | Tseng et al. |
| 2003/0019764 A1 | 1/2003 | Baldwin et al. |
| 2003/0024828 A1 | 2/2003 | Kondo et al. |
| 2003/0045502 A1 | 3/2003 | Kataoka et al. |
| 2003/0049163 A1 | 3/2003 | Malchesky et al. |
| 2003/0062068 A1 | 4/2003 | Ko et al. |
| 2003/0064427 A1 | 4/2003 | Felkner et al. |
| 2003/0087427 A1 | 5/2003 | Colton et al. |
| 2003/0089618 A1 | 5/2003 | Satoh et al. |
| 2003/0098283 A1 | 5/2003 | Katayose et al. |
| 2003/0141200 A1 | 7/2003 | Harada |
| 2003/0185704 A1 | 10/2003 | Bernard et al. |
| 2003/0219361 A1 | 11/2003 | Lee et al. |
| 2003/0230826 A1 | 12/2003 | Kawaguchi et al. |
| 2004/0004007 A1 | 1/2004 | Orolin et al. |
| 2004/0011665 A1 | 1/2004 | Koizumi et al. |
| 2004/0029761 A1 | 2/2004 | Wakamatsu et al. |
| 2004/0037737 A1 | 2/2004 | Marais et al. |
| 2004/0055896 A1 | 3/2004 | Anderson et al. |
| 2004/0060815 A1 | 4/2004 | Buckley et al. |
| 2004/0079791 A1 | 4/2004 | Kida et al. |
| 2004/0081705 A1 | 4/2004 | Gotou |
| 2004/0084325 A1 | 5/2004 | Weinberg et al. |
| 2004/0084326 A1 | 5/2004 | Weinberg et al. |
| 2004/0094406 A1 | 5/2004 | Sawada |
| 2004/0131695 A1 | 7/2004 | Hinze |
| 2004/0137078 A1 | 7/2004 | Najafi et al. |
| 2004/0154993 A1 | 8/2004 | Yanagihara et al. |
| 2004/0168909 A1 | 9/2004 | Larson |
| 2004/0168933 A1 | 9/2004 | Inoue |
| 2004/0171701 A1 | 9/2004 | Shaw |
| 2004/0172985 A1 | 9/2004 | Mamiya et al. |
| 2004/0177655 A1 | 9/2004 | Kodera et al. |
| 2004/0185311 A1 | 9/2004 | Muthuswamy et al. |
| 2004/0185313 A1 | 9/2004 | Halter et al. |
| 2004/0188248 A1 | 9/2004 | Sawa |
| 2004/0208940 A1 | 10/2004 | Selkon |
| 2004/0244537 A1 | 12/2004 | Runyon |
| 2004/0250323 A1 | 12/2004 | Arai et al. |
| 2004/0254744 A1 | 12/2004 | Shyu |
| 2004/0256317 A1 | 12/2004 | Yamada et al. |
| 2004/0265394 A1 | 12/2004 | Morris et al. |
| 2005/0000117 A1 | 1/2005 | Polegata |
| 2005/0054973 A1 | 3/2005 | Constantz et al. |
| 2005/0058013 A1 | 3/2005 | Warf et al. |
| 2005/0062289 A1 | 3/2005 | Cho et al. |
| 2005/0064259 A1 | 3/2005 | Coors |
| 2005/0067300 A1 | 3/2005 | Tremblay et al. |
| 2005/0074421 A1 | 4/2005 | Tanaka |
| 2005/0075257 A1 | 4/2005 | Scheper et al. |
| 2005/0101838 A1 | 5/2005 | Camillocci et al. |
| 2005/0109610 A1 | 5/2005 | Inamoto et al. |
| 2005/0121334 A1 | 6/2005 | Sumita |
| 2005/0126927 A1 | 6/2005 | Lindauer et al. |
| 2005/0126928 A1 | 6/2005 | Hung et al. |
| 2005/0129996 A1 | 6/2005 | Moulthrop et al. |
| 2005/0139465 A1 | 6/2005 | Kasuya et al. |
| 2005/0139808 A1 | 6/2005 | Alimi |
| 2005/0142157 A1 | 6/2005 | Alimi |
| 2005/0153858 A1 | 7/2005 | Anthony et al. |
| 2005/0155863 A1 | 7/2005 | Kovacs et al. |
| 2005/0161950 A1 | 7/2005 | Borden et al. |
| 2005/0178349 A1 | 8/2005 | Borden et al. |
| 2005/0178920 A1 | 8/2005 | Wilson |
| 2005/0183949 A1 | 8/2005 | Daly et al. |
| 2005/0183964 A1 | 8/2005 | Roberts et al. |
| 2005/0189234 A1 | 9/2005 | Gibson et al. |
| 2005/0189237 A1 | 9/2005 | Sano |
| 2005/0196462 A1 | 9/2005 | Alimi |
| 2005/0198963 A1 | 9/2005 | Wai et al. |
| 2005/0209518 A1 | 9/2005 | Sage et al. |

FOREIGN PATENT DOCUMENTS

| | | |
|---|---|---|
| EP | 0 368 812 A1 | 5/1990 |
| EP | 0 601 891 A1 | 6/1994 |
| EP | 0 636 581 | 7/1994 |
| EP | 0 740 329 A | 4/1997 |
| EP | 0889007 A1 | 4/1997 |
| EP | 0826636 A1 | 3/1998 |
| EP | 0841305 A2 | 5/1998 |
| EP | 0 949 205 A1 | 10/1999 |
| EP | 1 038 993 A | 9/2000 |
| EP | 1064845 A1 | 1/2001 |
| EP | 1065265 A1 | 1/2001 |
| EP | 1 074 515 A2 | 2/2001 |
| EP | 1 103 264 A2 | 5/2001 |
| EP | 1162176 A1 | 12/2001 |
| EP | 1314699 A1 | 5/2003 |
| EP | 1386887 A1 | 2/2004 |
| GB | 2253860 A | 9/1992 |
| GB | 2352728 A | 2/2001 |
| JP | 01194993 | 8/1989 |
| JP | 01218682 | 8/1989 |
| JP | 02149395 | 6/1990 |
| JP | 05-339769 A | 12/1993 |
| JP | 06-182345 | 7/1994 |
| JP | 05228474 | 9/1994 |
| JP | 05228475 | 9/1994 |
| JP | 06254567 | 9/1994 |
| JP | 06312183 | 11/1994 |
| JP | 06335685 | 12/1994 |
| JP | 07-000966 A | 1/1995 |
| JP | 07031981 | 2/1995 |
| JP | 07-075784 A | 3/1995 |
| JP | 07-155760 | 6/1995 |
| JP | 07-214063 | 8/1995 |
| JP | 07238640 | 12/1995 |
| JP | 07323289 | 12/1995 |
| JP | 08-001160 A | 1/1996 |
| JP | 08052476 | 2/1996 |
| JP | 08-061788 | 3/1996 |
| JP | 08164192 | 6/1996 |
| JP | 08326124 | 12/1996 |
| JP | 09025236 | 1/1997 |
| JP | 09-157173 A2 | 6/1997 |
| JP | 09-290269 | 11/1997 |
| JP | 10080686 | 3/1998 |
| JP | 10-128331 A2 | 5/1998 |
| JP | 10113664 | 5/1998 |
| JP | 11-151493 A * | 6/1999 |
| JP | 11-151493 A2 | 6/1999 |
| JP | 10192860 | 3/2000 |
| JP | 2001/079548 | 3/2001 |
| JP | 2000/084559 | 4/2001 |
| JP | 2001-096275 A | 4/2001 |
| JP | 2001/113276 | 6/2001 |
| JP | 2001-191076 A2 | 7/2001 |
| JP | 03-236315 B2 | 12/2001 |
| JP | 03-247134 B2 | 1/2002 |
| JP | 2002-059164 A | 2/2002 |
| JP | 03-299250 B2 | 7/2002 |

| | | |
|---|---|---|
| JP | 03-338435 B2 | 10/2002 |
| JP | 03-396853 B2 | 4/2003 |
| JP | 2003/236543 | 8/2003 |
| JP | 03-458341 B2 | 10/2003 |
| JP | 2004/049946 | 2/2004 |
| JP | 2004/216349 | 8/2004 |
| JP | 2004/223306 | 8/2004 |
| JP | 2004/223309 | 8/2004 |
| JP | 2004/223310 | 8/2004 |
| JP | 2004/232413 | 8/2004 |
| JP | 2005/013520 A2 | 1/2005 |
| JP | 2005/058848 A2 | 3/2005 |
| SU | 1296156 A | 3/1987 |
| WO | WO 96/02271 | 2/1996 |
| WO | WO 9601655 | 6/1996 |
| WO | WO 97/49638 A | 12/1997 |
| WO | WO 97046489 A1 | 12/1997 |
| WO | WO 98017588 A1 | 4/1998 |
| WO | WO 98/27013 | 6/1998 |
| WO | WO 98042625 A1 | 10/1998 |
| WO | WO 98058880 A1 | 12/1998 |
| WO | WO 99000588 A2 | 1/1999 |
| WO | WO 99028238 A1 | 6/1999 |
| WO | WO 00033757 A1 | 6/2000 |
| WO | WO 00076475 A1 | 12/2000 |
| WO | WO 01/13926 | 3/2001 |
| WO | WO 02/04032 A2 | 1/2002 |
| WO | WO 03000957 A1 | 6/2002 |
| WO | WO 03024491 A2 | 3/2003 |
| WO | WO 03/042111 A2 | 5/2003 |
| WO | WO 03/048421 A1 | 6/2003 |
| WO | WO 03076688 A2 | 9/2003 |
| WO | WO 03103522 A1 | 12/2003 |
| WO | WO 04076721 A1 | 9/2004 |
| WO | WO 04078654 A2 | 9/2004 |
| WO | WO 04079051 A1 | 9/2004 |
| WO | WO 04081222 A2 | 9/2004 |
| WO | WO 04082690 A1 | 9/2004 |
| WO | WO 04092571 A1 | 10/2004 |
| WO | WO 05003848 A1 | 1/2005 |
| WO | WO 05011417 A2 | 2/2005 |
| WO | WO 05020896 A2 | 3/2005 |
| WO | WO 05030651 A1 | 4/2005 |
| WO | WO 05061394 A1 | 7/2005 |
| WO | WO 05075581 A1 | 8/2005 |
| WO | WO 05080639 A1 | 9/2005 |
| WO | WO 05082176 A1 | 9/2005 |

OTHER PUBLICATIONS

International Search Report for PCT/US02/38861.
European Search Report for EP 1 293 481.
Supplementary European Search Report for EP 02 79 0029.
Ayliffe, "Working Party Report: Decontamination of minimally invasive surgical endoscopes and accessories," *Journal of Hospital Infection*, 45, 263-277 (2000).
Badia et al., "Saline Wound Irrigation Reduces the Postoperative Infection Rate in Guinea Pigs." *Journal of Surgical Research*, 63, 457-459 (1996).
Beckman, et al., "The free radical theory of aging matures," *Physiol. Rev.* 78, 547-581 (1998).
Chisholm, "Wound Evaluation and Cleansing." *Soft Tissue Emergencies*, 10(4), 665-672 (1992).
Dire, et al., "A Comparison of Wound Irrigation Solutions Used in the Emergency Department," *Ann Emerg Med.*, 19(6), 704-8 (1998).
Dyson et al., "Comparison of the Effects of Moist and Dry Conditions on Dermal Repair," *Journal for Investigative Dermatology*, 91(5), 434-439 (1988).
Erwin-Toth, et al., "Wound Care Selecting the Right Dressing," *Am J Nurs.*, 95(2), 46-51 (1995).
Field, et al., "Overview of Wound Healing in a Moist Environment," *Am J Surg.*, 167(1A), 2S-6S (1994).

Higgins, et a., "Wound dressings and Topical Agents." *The Diabetic Foot*, 12(1), 31-40, (1995).
Hinman, et al., "Effect of Air Exposure and Occlusion on Experimental Human Skin Wounds," *Nature*, 200, 377-379 (1963).
Hollander, et al., "Laceration Management," *Annals of Emergency Medicine*, 34(3), 356-367 (1999).
Horita, et al., "Healing of Fournier's gangrene of the scrotum in a haemodialysis patient after conservative therapy alone," *Nephrology Dialysis Transplantation*, 15 (3), 419-421 (2000).
Jeter, et al., "Wound Dressings of the Nineties: Indications and Contraindications," *Wound Healing*, 8(4), 799-816 (1991).
Koseki, et al., "Effect of mild heat pre-treatment with alkaline electrolyzed water on the efficacy of acidic electrolyzed water against *Escherichia coil* O157:H7 and *Salmonella* on lettuce," *Food Microbiology*, 21(5), 559-566 (2004).
Loshon, et al., "Analysis of the killing of spores of *Bacillus subtilis* by a new disinfectant, Sterilox," Journal of Applied Microbiology, 91, 1051-1058 (2001).
Madden, et al., "Application of Principles of Fluid Dynamics to Surgical Wound Irrigation," source unknown.
Marnett, "Oxyradicals and DNA damage," Carcinogenesis, 21, 361-370 (2000).
Martinez, "Sterilant for Human Wounds is Changing Patients' Lives" Infection Control Today, (2004).
Middleton, et al., "Comparison of a solution of super-oxidized water (Sterilox) with glutaraldehyde for the disinfection of bronchoscopes, contaminated *in vitro* with *Mycobacterium tuberculosis* and *Mycobacterium avium-intracellulare* in sputum," *Journal of Hospital Infection*, 45, 278-282 (2000).
Miranda-Altamirano et al., "Treatment of $2^{nd}$ and $3^{rd}$ Degree Burns in 48 Pediatric Patients Without Routine Antibiotics Routine Using New Super-oxidized Water Technology" Abstract for Meeting of the Texas Surgical Society, Apr. 1-3, 2005.
Moscati, et al., "Comparison of Normal Saline with Tap Water for Wound Irrigation," *American Journal of Emergency Medicine*, 16(4), 379-385 (1998).
Nakagawara, et al., "Spectroscopic characterization and the pH dependence of bactericidal activity of the aqueous chlorine solution," *Analytical Sciences*, 14(4), 691-698 (1998).
Ohno, et al., "Mediastinal Irrigation with Superoxidized Water After Open-Heart Surgery: The Safety and Pitfalls of Cardiovascular Surgical Application," *Surgery Today*, 30, 1055-1056 (2000).
Piaggesi, et al., "Sodium carboxyl-methyl-cellulose dressings in the management of deep ulcerations of diabetic foot," *Diabet Med.*, 18(4), 320-4 (2001).
Rodeheaver, et al., "Identification of the Wound Infection-Potentiating Factors in Soil," *American Journal of Surgery*, 128(1), 8-14, (1974).
Ruddy, et al., "Decontamination in Practice: Endoscopic decontamination: and audit and practical review," *Journal of Hospital Infection*, 50, 261-268 (2002).
Rutala, et al., "New Disinfection and Sterilization Methods," *Centers for Disease Control and Prevention (CDC): Emerging Infectious Diseases*, 7 (2), 348-353 (2001).
Sekiya, et al., "Treatment of Infectious Skin Defects or Ulcers with Electrolyzed Strong Acid Aqueous Solution," *Artificial Organs*, 21 (1), 32-38 (1997).
Selkon, et al., "Evaluation of the antimicrobial activity of a new super-oxidized water, Sterilox®, for the disinfection of endoscopes," *Journal of Hospital Infection*, 41, 59-70 (1999).
Shen, et al., "Interactions of selenium compounds with other antioxidants in DNA damage and apoptosis in Human normal keratinocytes," *Cancer Epidemiol Biomarkders Prev.*, 10, 385-390 (2001).
Shetty, et al., "Evaluation of microbicidal activity of a new disinfectant: Sterilox® 2500 against Clostridium difficile spores, Helicobacter pylori, cancomycin resistant *Enterococcus* species, Candida albicans and several *Mycobacterium* species," *Journal of Hospital Infection*, 41, 101-105 (1999).
Shimmura, et al., "Acidic Electrolyzed Water in the Disinfection of the Ocular Surface," *Experimental Eye Research*, 70(1), 1-6 (2000).
Singer, et al., "Evaluation and Management of Traumatic lacerations," *New England Journal of Medicine*, 1142-1148 (1997).

Solovyeva, et al., "Cleaning effectiveness of root canal irrigation with electrochemically activated anolyte and catholyte solutions: a pilot study," *International Endodontic Journal*, 33, 494-504 (2000).

Stevenson, et al., "Cleansing the Traumatic Wound by High Pressure Syringe Irrigation." *JACEP*, 5(1), 17-21 (1976).

Tanaka, et al., "Antimicrobial activity of superoxidized water" *Journal of Hospital Infection*, 34, 43-49 (1996).

Upright, et al., "Evaluation of Mesalt dressings and continuous wet saline dressings in ulcerating metastatic skin lesions," *Cancer Nursing*, 17(2), 149-155 (1994).

Venkitanarayanan, et al., "Efficacy of Electrolyzed Oxidizing Water for Inactivating *Escherichia coli* O157:H7, *Salmonella enteritidis*, and *Listeria monocytogenes*," *Applied and Environmental Microbiology*, 65 (9), 4276-4279 (1999).

Veves, et al., "A randomized, controlled trial of Promogran (a collagen/oxidized regenerated cellulose dressing) vs standard treatment in the management of diabetic foot ulcers,"*Arch Surg.*, 137(7), 822-7 (2002).

Winter, "Formation of the Scab and the Rate of Epithelization of Superficial Wounds in the Skin of the Young Domestic Pig," *Nature*, 193, 293-294 (1962).

Xakellis, et al., "Hydrocolloid versus saline-gauze dressings in treating pressure ulcers: a cost-effectiveness analysis," *Arch Phys Med Rehabil.*, 73(5), 463-9 (1992).

Yahagi, et al., "Effect of Electrolyzed Water on Wound Healing," *Artificial Organs*, 24 (12), 984-987 (2000).

Zinkevich, et al., "The effect of super-oxidized water on *Escherichia coli*," *Journal of Hospital Infection*, 46, 153-156 (2000).

Communication from the International Searching Authority dated Oct. 4, 2005 for PCT/US2004/043961 (including partial international search report).

Arrigo, et al., "Cytotoxic effects induced by oxidative stress in culture mammalian cells and protection provided by Hsp27 expression," (2005) (source unknown).

Bari, et al., "Chemical and irradiation treatments for killing *Escherichia coil* O157:H7 on alfalfa, radish, and mung bean seeds," *J Food Prot.*, 66(5), 767-74 (2003).

Bari, et al., "Effectiveness of electrolyzed acidic water in killing *Escherichia coli* O157:H7, Salmonella enteritidis, and Listeria monocytogenes on the surfaces of tomatoes," *J Food Prot.*, 66(4), 542-8 (2003).

Boulton, *The Diabetic Foot.* "Diabetes: Clinical Management," Chapter 26, 293-306.

Carlson, "Redox media as a factor in destroying germs," *Schriftenreihe des Vereins fuer Wasser-, Boden- und Lufthygiene*, 31, 21-39 (1970).

Carton, et al., "Hypotonicity induces membrane protrusions and actin remodeling via activation of small GTPases Rac and Cdc42 in Rat-1 fibroblast," *Am. J. Physiol. Cell. Physiol.*, 285, C935-C944 (2003).

Chernomorskii, "Diagram of the electrochemical stability of water", *Zhurnal Fizicheskoi Khimii*, 51(4), 924-925 (1977).

De Grey, "Reactive oxygen species production in the mitochondrial matrix: implications for the mechanism of mitochondrial mutation accumulation," *Rejuvenation Res.*, 8(1), 13-17 (2005).

Dressler, "Standards and Histogram Interpretation in DNA Flow Cytometry," *Methods in Cell Biology*, 41, 241-262 (1994).

Fabrizo, et al., "Comparison of electrolyzed oxidizing water with various antimicrobial interventions to reduce Salmonella species on poultry," *Poult. Sci.*, 81(10), 1598-605 (2002).

Flint, et al., "Virus cultivation detection and genetics," Chapter 2, *Principles of Virology, Molecular Biology, Pathogenesis and Control*, ASM Press 2000; 32.

Fraise, "Choosing disinfectants," *J Hosp infect*, 43, 255-264 (1999).

Fraga, et al., "Ascorbic acid protects against endogenous oxidative DNA damage in human sperm," *Proc. Natl. Acad. Sci USA*, 88, 11003-11006 (1991).

Frippiat, et al., "Subcytotoxic $H_2O_2$ stress triggers a release of transforming growth factor-beta, which induces biomarkers of cellular senescence of human diploie fibroblast," *J. Biol. Chem.* 276, 2531-2537 (2001).

Fromin, et al., "Participation of water [hydroxyl ions] in oxidation-reduction processes," *Sostoyanie Rol Vody Biol. Ob'ektakh, Simp., Tiflis*, 120-131 (1967).

Gao, et al., "Observation on the effect of disinfection to HBs Ag by electrolyzed oxidizing water," *Zhonghua Liu Xing Bing Xue Za Zhi*, 22, 40-42 (2001).

Goberdham, et al., "A biomarker that identifies senescent human cell in culture and in aging skin *in vivo,"Proc. Natl. Acad. Sci. USA*, 92, 9663-9667 (1995).

Guitierrez, et al., "Production de agents biologicos par alas terapias genicas y celulares en humanos," *Diagnostico molecular en medicina*, 265-291 (2003).

Harada, "Behavior of hydrogen peroxide in electrolyzed anode water," *Biosci. Biotechnol Biochem.*, 66(9), 1783-91 (2002).

Hatto, et al., "The physiological property and function of the electrolyzed-ionized calcium Aquamax on water molecular clusters fractionization," *Artif. Organs*, 21(1), 43-9 (1997).

Hayashi, et al., "Successful treatment of mediastinitis after cardiovascular surgery using electrolyzed strong acid water aqueous solution," *Artif Organs*, 21, 39-42 (1997).

Horiba, et al., "Bactericidal effect of electrolyzed neutral water on bacteria isolated from infected root canals," *Oral Surg Oral Med Oral Pathol Oral Radiol Endod*, 87, 83-87 (1999).

Inoue, et al., "Trial of electrolyzed strong acid aqueous solution lavage in the treatment of peritonitis and intraperitoneal abscess," *Artif Organs*, 21, 28-31 (1997).

Ivanova, et al., "Mechanism of the extracellular antioxidant defend," *Experimental pathology and parasitology*, 4, 49-59 (2000).

Iwasawa, et al., "Bactericidal effect of acidic electrolyzed water—comparison of chemical acidic sodium hydrochloride (NaOCl) solution," *Kansenshogaku Zasshi,*; 70(9), 915-22 (1996).

Iwasawa, et al., "The influence of pH on bactericidal effects of strong acidic electrolyzed water," *Bokin Bobai*, 30(10), 635-643, (2002).

Kaufman, "Preventing Diabetic Foot Ulcers," *Derm. Nurs.*, 6(5), 313-320 (1994).

Kiura, et al., "Bactericidal activity of electrolyzed acid water from solution containing sodium chloride at low concentration, in comparison with that at high concentration," *J Microbiol Methods*, 49(3), 285-93 (2002).

Kim, et al., "Efficacy of electrolyzed oxidizing water in inactivating Salmonella on alfalfa seeds and sprouts," *J Food Prot.*, 66(2), 208-14 (2003).

Kim, et al., "Roles of oxidation-reduction potential in electrolyzed oxidizing and chemically modified water for the inactivation of food-related pathogens," *J Food Prot*, 63, 19-24 (2000).

Kimbrough, et al., "Electrochemical removal of bromide and reduction of THM formation potential in drinking water," *Water Res.*, 36(19), 4902-6 (2002).

Kitaoka, "On the electrolytic separation factor of tritium," *Radioisotopes*, 30(5), 247-52 (1981).

Koseki, et al., "Effect of nitrogen gas packaging on the quality and microbial growth of fresh-cut vegetables under low temperatures," *J Food Prot.*, 65(2), 326-32 (2002).

Koseki, et al., "Decontaminative effect of frozen acidic electrolyzed water on lettuce," *J Food Prot.*, 65(2), 411-4 (2002).

Koseki, et al., "Decontamination of lettuce using acidic electrolyzed water," *J Food Prot.*, 64(5), 652-8 (2001).

Koseki, et al., "Prediction of microbial growth in fresh-cut vegetables treated with acidic electrolyzed water during storage under various temperature conditions," *J Food Prot.*, 64(12), 1935-42 (2001).

Laing, "Diabetic Foot Ulcers," *Am J Surg*, 167, 31S-26S (1994).

Len, et al., "Ultraviolet spectrophotometric characterization and bactericidal properties of electrolyzed oxidizing water as influenced by amperage and pH," *J Food Prot*, 63, 1534-1537 (2000).

Len, et al., "Effects of storage conditions and pH on chlorine loss in electrolyzed oxidizing (EO) water," *J Agric Food Chem*, 50, 209-212 (2002).

Li, et al., "Preliminary study of microbiocide effect and its mechanism of electrolyzed oxidizing water," *Zhonghua Liu Xing Bing Xue Za Zhi*, 7, 95-98 (1996).

Mangram, et al., "Guideline for prevention of surgical site infection," *Infection Control and Hospital Epidemiology*, 1999, 20(4), 247-278 (1999).

Michida, et al., "Biomimetic oxidation of diphenyl sulfide with electrochemical P-450 model system in CH2C12 treated with alkaline solution," *Yakugaku Zasshi*, 119(10), 780-5 (1999).

Minimal Access Therapy Decontamination Working Group, "Decontamination of minimally invasive surgical endoscopes and accessories," *J Hosp. Infect*, 45, 263-277 (2000).

Miyamoto, et al., "Effectiveness of acidic oxidative potential water in preventing bacterial infection in islet transplantation," *Cell Transplant*, 8, 405-411 (1999).

Model, et al., "Effectiveness of electrolyzed oxidized water irrigation in a burn-wound infection," *J Trauma Injury, Infection, and Critical Care*, 49, 511-514 (2000).

Morita, et al., "Disinfection potential of electrolyzed solution containing sodium chloride at low concentrations," *J Virol Methods*, 85, 163-174 (2000).

Moyer, et al., "Modulation of human fibroblast Gap junction intercellular communication by Hyaluronan," *J. Cell. Biol.* 196, 165-170 (2003).

Naderi, et al., "Oxidative stress-induced apoptosis in dividing fibroblast involves activation of p38 MAP kinase and over expression of Bax: Resistance of quiescent cells to oxidative stress," *Apoptosis*, 8, 91-100 (2003).

Nagamatsu, et al., "Application of electrolyzed acid water to sterilization of denture base part 1. Examination of sterilization effects on resin plate," *Dent. Mater J*, 20(2), 148-55, (2001).

Nagamatsu, et al., "Durability of bactericidal activity in electrolyzed neutral water by storage," *Dent Mater J*, 21, 93-104 (2002).

Nakae, et al., "Effectiveness of electrolyzed oxidized water irrigation in a burn-wound infection model," *J Trauma*, Sept.; 49(3): 511-4 (2000).

Nakagawa, et al., "Effect of rinsing hydrocolloid impressions using acidic electrolyzed water on surface roughness and surface hardness of stone models," *J Oral Sci.*, 44(3-4), 141-6 (2002).

Nelson, "Newer technologies for endoscope disinfection: electrolyzed acid water and disposable-component endoscope systems," *Gasatrointest Endosc Clin N Am*, 10, 319-328 (2000).

Ogino, et al., "Treatment for abdominal aortic graft infection: irrigation with electrolyzed strong aqueous acid, in-situ grafting, and omentoplasty," *Thorac Cardiovasc Surg*, 48(1), 43-44 (2000).

Okubo, et al., "Cytotoxicity and microbicidal activity of electrolyzed strong acid water and acidic hypochlorite solution under isotonic conditions," *Kansenshogaku Zasshi*, 73(10), 1025-31 (1999).

O'Neill, "Physiological significance of volume-regulatory transporters,"*Am. J. Physiol.* 276, C995-C1001 (1999).

Oomori, et al., "The efficiency of disinfection of acidic electrolyzed water in the presence of organic materials," *Anal Sci*, 16, 265-369 (2000).

Ottender, et al., "Correlation of DNA adduct levels with tumor incidence: carcinogenic potency of DNA adducts," *Mutat. Res.*, 424, 237-247 (1999).

Park, et al., "Antimicrobial effect of electrolyzed water for inactivating Campylobacter jejuni during poultry washing," *International Journal of Food Microbiology*, 72(1-2), 77-83 (2002).

Park, "Effectiveness of electrolyzed water as a sanitizer for treating different surfaces," *J Food Prot.*, 65(8), 1276-80 (2002).

Park, et al., "Effects of chlorine and pH on efficacy of electrolyzed water for inactivating Escherichia coli O157:H7 and Listeria monocytogenes," *International Journal of Food Microbiology*, 91(1), 13-18 (2004).

Powis, et al., "Redox signaling and the control of cell growth and death," *Pharmacol Ther.*, 68, 149-173 (1995).

Russell, "The effect of electrolyzed oxidative water applied using electrostatic spraying on pathogenic and indicator bacteria on the surface of eggs," *Poult. Sci.*, 82(1), 158-62 (2003).

Sakai, "Development of ionic electrolyzed water and its utilities. The preparation of ionic electrolyzed water and its application to disinfection," *Kurin Tekunoroji* (1996), 6(3), 53-57 (1996).

Sakashita, et al., "Antimicrobial effects and efficacy on habitually hand-washing of strong acidic electrolyzed water—a comparative study of alcoholic antiseptics and soap and tap water", *Kansenshogaku Zasshi* 76, 373-377 (2002).

Sanders, "Diabetes Mellitus: Prevention of Amputation," *J Am Pod Med Assoc*, 84(7), 322-328 (1994).

Sawada, "Complete electrolysis using a microflow cell with an oil/water interface." *Anal Chem.*, 74(5), 1177-81 (2002).

Severino, et al., "Is β-galactosidase staining a marker of senescence in vitro and in vivo?" *Exp. Cell. Res.*, 257, 162-171 (2000).

Sharma, et al., "Treatment of *Escherichia coli* O157:H7 inoculated alfalfa seeds and sprouts with electrolyzed oxidizing water," *International Journal of Food Microbiology*, 86(3), 231-237 (2003).

Shirahata, et al., "Electrolyzed-reduced water scavenges active oxygen species and protects DNA from oxidative damage," *Biochem. Biophys. Res. Commun.*, 234(1), 269-74 (1997).

Smirnov, et al., "Electron exchangers and electron- and ion-exchangers and their use in a water treatment system," *Khim. Aktiv. Polim. Ikh Primen*, 259-262 (1969).

Soto, et al., "Bacterial sulfate production by biodesulfurization of aromatic hydrocarbons, determined by ion chromatography," *J Chromatogr A*, 824(1), 45-52 (1998).

Stein, "SV-40-transformed human fibroblasts: evidence for cellular aging in pre-crises cells ," *J Cell, Physiol*, 125, 36-44 (1985).

Sumita, "Characteristics and use of acidified water from redox water generator," *Shokuhin Kogyo*, 40(10), 29-36 (1997).

Suzuki, "Novel products generated from 2'-deoxyguanosine by hypochlorous acid or a myeloperoxidase—$H_2O_2$-Cl-system: identification of diimino-imidazole and amino-imidazolone nucleosides," *Nucleic Acids Res.*, 30, 2555-2564 (2002).

Tanaka, et al., "The use of electrolyzed solutions for the cleaning and disinfecting of dialyzers" *Artif. Organs*, 24(12), 921-8 (2000).

Tanaka, et al., "Molecular basis of antiapoptotic effect of immunophilin ligands on hydrogen peroxide-induced apoptosis in human glioma cells," *Neurochem Res.*, 29(8), 1529-36 (2004).

Takeshita ,et al., "Influence of free residual chlorine concentration and pH on bactericidal effects of electrolyzed water," *Bokin Bobai*, 29(2), 69-72 (2001).

Takeyoshi, et al., "Primary eye irritation and 5-day cumulative skin irriation studies of super oxidized water in rabbits," *Oyo Yakuri*, 48(3), 173-177 (1994).

Tateno, et al., "MT-4 plaque formation can distinguish cytopathic substypes of the human immunodeficiency virus (HIV)," *Virology*, 167, 299-301 (1988).

Valko, et al., "Role of oxygen radicals in DNA damage and cancer incidence," *Mol Cell Biochem*, 266, 37-56 (2004).

Van Britsom, et al., "A rapid method for the detection of uranium in surface water," *Sci. Total Environ.*, 173-174, 83-9 (1995).

Yang, et al., "The effect of pH on inactivation of pathogenic bacteria on fresh-cut lettuce by dipping treatment with electrolyzed water," *Journal of Food Science*, 68(3), 1013-1017 (2003).

Yoshimoto, et al., "Virucidal effect of super oxidized water" *Kagaku Ryoho no Ryoiki*, 12(7), 1337-1342 (1996).

Young, et al., "Mechanisms of killing of *Bacillus subtilis* spores by hypochlorite and chlorine dioxide," *J Appl Microbiol*, 95, 54-67 (2003).

Zhang, et al., "Antioxidant superoxide dismutase attenuates increased endothelial permeability induced by platelet activating factor," *Soc Gynecol Investig.* 10, 5-10 (2003).

International Search Report in PCT/US2004/043961 (Nov. 25, 2005).

* cited by examiner (A)

(B)

ELECTROLYTIC CELL FOR PRODUCING CHARGED ANODE WATER SUITABLE FOR SURFACE CLEANING OR TREATMENT, AND METHOD FOR PRODUCING THE SAME AND USE OF THE SAME

BACKGROUND OF THE INVENTION

1. Field of the Invention

The present invention is related to a method for surface cleaning or treatment of semiconductors, glass, or resins, and device for producing electrically charged water as utility water for the above methods, more particularly a technique for providing an electrolysis cell, which can produce electrically charged water suitable for surface cleaning or treatment without using chemical in consideration of environmental protection. The electrically charged water produced by using the electrolysis cell also has antimicrobial activates, and is suitable for cleaning and sterilizing medical devices for which high cleanliness is required.

2. Description of the Related Art

Electrolysis cell using ion exchange membrane, as shown FIG. 1, facilitates the electrolysis of water with low conductivity such as RO water treated using a reverse osmosis membrane pure water, and ultra pure water. In this cell, a fluorinated cation exchange membrane 5 is usually used.

And then an anode electrode 4 in the anode cell 1 and a cathode electrode 9 in the cathode cell 6 are closely attached to the membrane 5. The notation 2 denotes the anode chamber inlet, 3 denotes anode chamber outlet, 7 denotes the cathode chamber inlet, and 8 denotes the cathode chamber outlet.

The ion exchange group in fluorinated cation exchange membrane 5 shown in FIG. 1 is known to enhance the dissociation even in the pure water according to the reaction (1).

$$-SO_3H \rightarrow -SO_3^- + H^+ \quad (1)$$

The dissociated hydrogen ions increase the electro conductivity of pure water, which contains no impurities, and then decrease the electrolysis voltage.

Next, the reaction (2) and (3) proceed when pure water is electrolyzed using the cell shown in FIG. 1.

At anode

$$2H_2O \rightarrow 2H^+ + O_2 + 2e^- \quad (2)$$

At cathode

$$2H^+ + 2e^- \rightarrow H_2 \quad (3)$$

These reactions increase the oxygen concentration in the anode solution and the hydrogen concentration in the cathode solution, while leaving the essential properties of electrolytic water unchanged.

In other words, the charged water produced using electrolysis cell shown in FIG. 1 may not be suitable for the surface cleaning or treatment of semiconductors, glass, or resins.

In order to enhance the cleaning or surface treatment efficacy, anode water is required to be more oxidative and/or acidic and cathode water is required to be more reductive and/or alkaline. However, the electrolysis cell shown in FIG. 1 is difficult to produce the effective solutions.

For example, the oxidation and reduction potential (hereinafter abbreviated as ORP) of anode water is from 200 to 300 mV (vs., Ag/AgCl) and pH is around neutral: the ORP of normal pure water is around 200 mV.

The three-chamber cell shown in FIG. 2 is designed to solve the problem mentioned above, where the middle chamber 111 is added between the anode chamber 11 and the cathode chamber. 16. Using the three-chamber cell easily electrolyzes pure water or ultra pure water.

Referring to FIG. 2, the three-chamber cell has the chamber 11 and 111 separated by the ion exchange membrane 151, chamber 16 and 111 separated by the ion exchange membrane 152, the middle chamber 111 filled with ion exchange resins as a solid electrolyte, the middle chamber inlet 112 and outlet 113, cathode 19 and anode 14 provided in suchaway to be closely attached to the ion exchange membrane 151 and 152, respectively, the anode camber inlet 12 and outlet 13, and the cathode chamber inlet 15 and 17.

The three-chamber cell has the following merits. Reductive species such as dissolved hydrogen gas produced in the cathode chamber 16 are likely to migrate into the anode chamber 11 though the ion exchange membrane 5 when the cell depicted in FIG. 1 is used. However, the middle chamber 111 in the three-chamber cell control the diffusion of reductive species from the cathode chamber 16 to the anode chamber 11 and then the more strongly oxidative anode water can be obtained. In the cell shown in FIG. 2, migration of hydrogen ions formed on the anode 14 toward the cathode 19 is limited, and then the electrolysis reaction (4) takes place in addition to the reaction (3):

$$H_2O + 2e^- \rightarrow \tfrac{1}{2}H_2 + OH^- \quad (4)$$

This reaction suggests that the pH of cathode water tends to shift to the alkaline region.

In another viewpoint, these phenomena suggest that hydrogen ions formed in the anode chamber 11 in the reaction (1) remain partly in that chamber.

In the three-chamber cell shown in FIG. 2 the anode solution, therefore, is likely to be charged with the hydrogen ions, whiles the cathode water is charged with hydroxide ions.

Electrochemical analytical methods are suitable for monitoring charges or the like to experimentally confirm the phenomena mentioned above. For example, the changes in measured values can be monitored by a pH sensor equipped with a glass electrode or ORP sensor which measure the oxidation-reduction potential of platinum electrode surface as a standard of a silver/silver chloride electrode. These sensors, following potential changes in the electrodes as the index, are suitable for confirming charges of electrolytic water. A temperature of the electrolytic water is usually kept at from 18 to 24° C. during measurement (the temperature in the following examples was kept at the almost same levels).

SUMMARY OF THE INVENTION

The charged electrolytic water produced using pure water functions as cleaning/surface treatment reagents for semiconductors, liquid crystal glass and hard disk glass or cleaning/sterilizing reagents for medical devices. A decontamination mechanism using electrolytic solutions is simply explained as follows.

Some contaminants are adhered to the surface of the device mentioned above by electrostatic or ionic attractive forces as schematically shown in FIG. 3, where (A) indicates the contaminated surface and (B) indicates the cleaned surface: the surface of substrate is supposed to be positively charged and contaminants are supposed to be negatively charged. When the contaminated substance is immersed in the effectively charged anode water, the negatively charges on the contaminants surface reacts with excess hydrogen ions in the anode water. Thus the surface charges are partly neutralized to reduce the bonding forces and thereby to facilitate cleaning. Conversely, when the contaminants are positively charged, the negative charges on the contaminated substance surface disappear to reduce the bonding forces. On the other hand, in the case of ionic contaminants, when the contaminated substance is immersed in anode water with excessive hydrogen ions, the anionic contaminants on the surface are likely to dissolve and then migrate to the anode solution to cancel the excessive charge. Using electrolytic water increases thus cleaning efficacy.

Anodic electrolysis of pure water produces the hydrogen ions according to the reaction (2), where no anion is present as counter ion, unlike acidic solutions prepared by adding acid such as hydrochloric acid or sulfuric acid. The anode water produced by electrolyzing pure water exhibits that the solution is charged. Moreover, the hydrogen ion by itself is an electron acceptor and so exhibits one of oxidizing species. So, the oxidation-reduction potential of anode water tends to shift to noble side. In other words, the ORP sensor indicates a plus value.

When the three-chamber cell depicted in FIG. 2 is used, the anode water is not necessarily sufficient for actual cleaning or surface treatment, although the theoretical consideration mentioned above appears to be very promising. So improving the cell is very important to apply to actual use.

More specifically, the important factors for producing effective charged water are an apparent current density (current (A)/apparent area of whole electrode ($cm^2$), a fluid velocity along the electrode surface, and an true current density (effective current density=current (A)/true area of the electrode ($cm^2$)). As the fluid velocity increases, the hydrogen ions and other electrolytic species produced on the electrode surface migrate faster to electrolytic water and then strangely charged water can be produced.

The inventors of this invention have found that it is important to pass water not only over the back side of electrode but also over the front side of electrode, based on the study to improve charged water production efficacy.

This result has led to the development of new methods for improving surface cleaning or treatment performance in semiconductors, glass, resins or the like, and of the apparatus (electrolytic cell) of the present invention which can efficiently produce the charged water with an excellent performance described above.

The invention has the following characteristic constituents to achieve the above objects.

(1) An electrolytic cell for producing charged anode water suitable for surface cleaning or treatment, including cathode, middle and anode chambers, a fluorinated cation-exchange membrane provided to separate cathode and middle chambers from each other, A cathode closely attached to the cation-exchange membrane on the side facing the cathode chamber, and a middle chamber filled with fluorinated cation-exchange resins, provided on the other side of the cation-exchange membrane, the cation-exchange resins being arranged in such a way to come into contact with the fluorinated cation-exchange membrane in the cathode chamber side and with the anode in the anode chamber side, wherein the feed water is fed into the middle chamber and passed through the fluorinated cation-exchange resins to be recovered as the charged anode water.

A shape of the fluorinated cation-exchange resin in this invention is not limited. It may be granular or fibrous, the former being more preferable.

The term "surface cleaning" used in this specification means an operation to remove contaminants from the surface and "surface treatment" means an operation to change surface composition or the like of a substance, e.g., glass, having ions, e.g., $Na^+$, $K^+$, and $H^+$, bonded in the bonding network of Si—O. Phenomena of the migration of $Na^+$ ions in glass were observed. When $Na^+$ ions present in the vicinity of the surface are removed, or more specifically ion-exchanged on the surface, the surface is prevented from roughing caused by the $Na^+$ ions. This process means the surface treatment, which is different form, the removal of foreign particles or impurity ions form the surface.

The ion-exchange membrane is usually cation-exchange membrane, preferably fluorinated cation-exchange membrane. It is essential for the present invention that the anode to be used in combination with the ion-exchange resins (cation-exchange resins) is a porous electrode or electrode having an ineffective area.

(2) The electrolytic cell for producing charged anode water suitable to surface cleaning or treatment according to the invention (1), wherein a porous anode is provided, and the middle chamber has an inlet but no outlet for the feed water to be treated and the anode chamber has an outlet for treated water but no inlet for the feed water.

(3) An electrolytic cell for producing charged anode water for surface cleaning or treatment, including cathode, middle and anode chambers, a fluorinated cation-exchange membrane provided to separate the cathode and middle chambers from each other, cathode closely attached to the cation-exchange membrane on the side facing the cathode chamber, cation exchange resins contained in the middle chamber and arranged to come into contact with the cation-exchange membrane on the opposite side facing the middle chamber, another fluorinated cation-exchange resins contained in the compartment between the fluorinated cation exchange membrane and the anode, wherein the feed water is passed over the anode surface and electrolytic water discharged from the anode chamber is recovered as the charged anode water.

(4) The electrolytic cell for producing charged anode water suitable for surface cleaning or treatment according to the invention (3), wherein a cation-exchange membrane is arranged in the middle chamber to divide the chamber into first middle chamber on the cathode chamber side and a second middle chamber on the anode chamber side.

(5) The electrolytic cell for producing charged anode water suitable for surface cleaning or treatment according to one of the inventions (1) to (4), whereon holes in the porous anode have a total area of 10% or more of a whole electrode area.

The holes are preferably arranged evenly on the entire electrode plane. Each hole preferably has an area of 1 $mm^2$ or more in consideration of passing efficiency of the anode water.

The anode for the present invention preferably has holes having an area 1 $mm^2$ or more, because a granular cation-exchange resin, when used, tends to pass through the holes, as its diameter is generally 1 mm or so, frequently 2 to 4 mm. However, a porous electrode having a large hole area is serviceable for a resin, e.g., fluorinated cation-exchange resins, which swell in pure water to have a higher friction coefficient between theres in particles. More specifically, DuPont' Nafion NR50 is preferable resin. A fluorinated one is preferable in consideration of resistance of the cation-exchange resin to oxidation reaction. More specifically, Du Pont' Nafion NR50 is preferable resin (6) The electrolytic cell for producing charged anode water suitable for surface cleaning or treatment according to one of the inventions (1) to (4), wherein the electrode has an ineffective area, which has no contribution to electrolysis, of 10% or more of the whole electrode area.

(7) The electrolytic cell for producing charged anode water suitable for surface cleaning or treatment according to one of the inventions (1) to (6), wherein a mechanism of controlling position of the anode in the direction of current flowing towards to cation-exchange resin is provided.

(8) The electrolytic cell for producing charged anode water suitable for surface cleaning or treatment according to one of the inventions (1) to (7), wherein the cation exchange resin is fluorinated one.

(9) A method of using charged anode solution produced by the electrolytic cell according to one of the inventions (1) to (8) for surface cleaning or treatment of an object.

(10) A method using charged anode water produced by the electrolytic cell according to the inventions (1) to (9), wherein feed water is pure water or ultra pure water. Pure water or ultra pure water means water having the resistivity of $0.1 M\Omega/cm$ or more.

(11) The method using charged anode water according to the invention (10), wherein the object to be cleaned or treated is a semiconductor, glass, or resin product.

(12) A method using charged anode water according to the invention (10), wherein the object to be cleaned or treated is a medical device.

(13) A method using charged anode solution produced by the electrolytic cell according to one of the inventions (1) to (9), wherein the feed water to the anode chamber is cooled to increase the ozone concentration in the anode water.

(14) A method using charged anode water produced by the electrolytic cell according to one of the inventions (1) to (4), (6) and (8) to (12), wherein the anode is directly cooled to increase the ozone concentration in the charged anode water.

The porous anode or cathode in each aspect of the present invention described above means that the planar electrode is structured to have holes (hereinafter referred to as "opening") through which water can pass on both front and backside. These openings are preferably arranged in such a way to make resistance to water flow uniform throughout the plane, and normally distributed evenly on the plane. Adequate size of the opening and ratio of the total opening area to the whole planar electrode area changes depending on the current density and resistance to water flow so that the apparatus is required to secure, and are not determined sweepingly.

These factors greatly depend on the electrode hole structure and ion-exchange resin size: increasing opening size and/or ion-exchange resin size decreases the resistance to water flow and, at the same time, increases the effective current density because contact area between the electrode and resins decreases. However, it is difficult to hold the ion-exchange resins between the membrane and electrode, when opening size increases excessively. Therefore, there is an optimum shape for each of opening and ion-exchange resin.

As discussed above, the electrolytic anode water, produced by passing pure water through the electrolysis cell having a controlling function, has the characteristics described in the examples.

DETAILED DESCRIPTION OF THE REFERRED EMBODIMENTS

The three-chamber type electrolytic cell to which the present invention is applied is described as follows.

Embodiment 1

Figure 1:
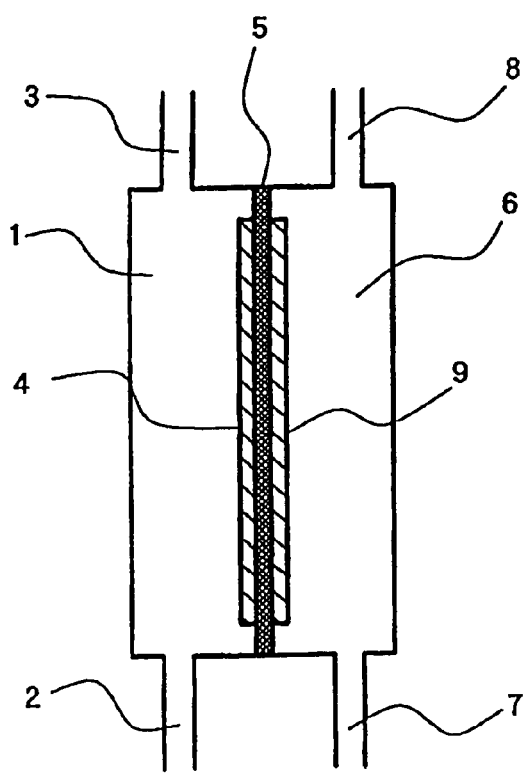
FIG. 1 shows the schematic cross-sectional view of the conventional electrolytic cell for electrolysis using ion-exchange separator.
Figure 2:
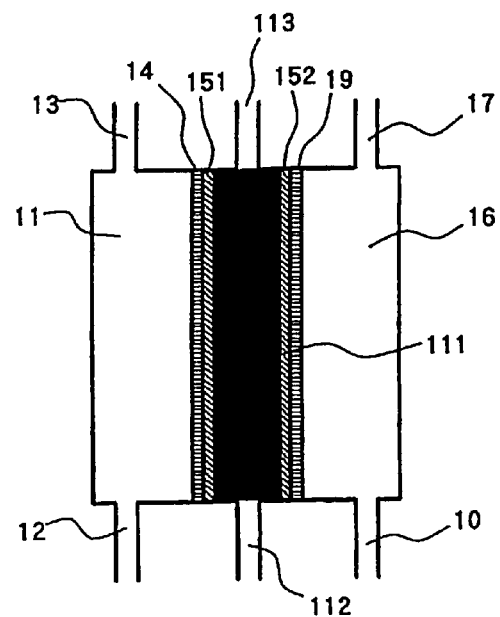
FIG. 2 shows the schematic cross-sectional view of the conventional three-chamber type electrolytic cell.
Figure 3:
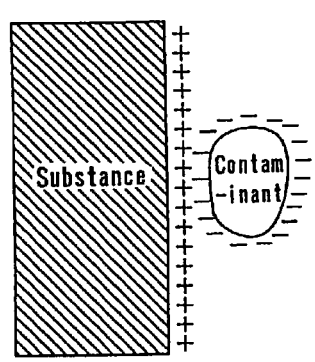
FIG. 3 describes the decontamination mechanism using the electrolytic water, where (A) describe the situation before treatment and (B) that after treatment.
Figure 3:
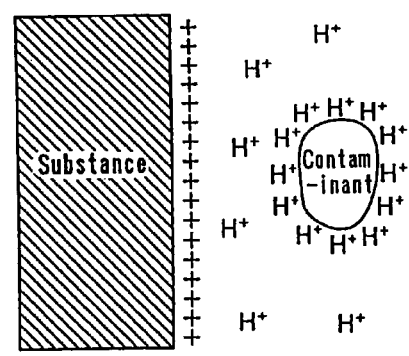
Figure 4:
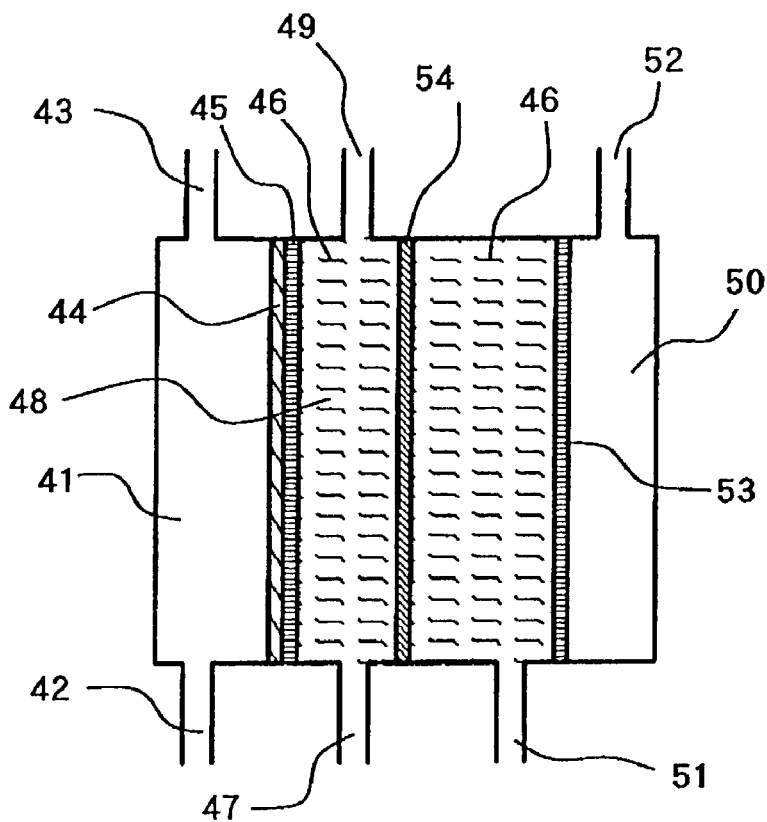
FIG. 4 shows the schematic cross-sectional view of the electrolytic cell in the first embodiment of the present invention.

FIG. 4 illustrates the new three-chamber type electrolytic cell made by improving the conventional three-chamber cell in which the perforated electrode plate shown in the drawing is used.

The anode 53 was closely attached to the cation-exchange membrane before the improvement. Therefore, the electrolytic water flowed along the anode plane, and the electrolysis reaction proceeded between the electrode and ion exchange membrane. As a result, the electrolysis products were formed first between the electrode and ion exchange membrane, and then moved toward the backside of electrode by diffusion or the like.

In the present invention, on the other hand, the anode is perforated to provide the passages for electrolytic water passing over the electrode surface, in order to utilize the electrolysis product more efficiently. As a result, the electrolytic water flows not only on the electrode surface but also thorough the holes opened in the electrode. The relationship between opening size and ion-exchange resin size is very important. It is necessary to increase the opening size of electrode, in order to water flow rate. However, it is difficult to hold the ion-exchange resins between the membrane and electrode, when the opening size increases excessively as compared with ion-exchange resin size. The ion-exchange resin is either spherical or fibrous, the former being generally more preferable. Its diameter is ranging from around 1 mm when it is small to 2 to 4 mm when it is large. Therefore, an excessively large opening size in comparison with ion-exchange resins is undesirable. The ion-exchange resin preferably has a large diameter to reduce resistance to water flow. Moreover, the fluorinated cation-exchange resin is preferable, because it comes into contact with the anode.

Moreover, the fluorinated cation exchange resins greatly decrease the electrolysis voltage and thus facilitate the electrolysis of pure water. The Nafion NR50 made by Du Pont is preferable fluorinated cation-exchange resin, as mentioned earlier.

It is possible to control the current density by changing the contact area between the fluorinated cation-exchange resin and anode. The fluorinated cation-exchange resin naturally swells in pure water. So its diameter increases with swelling and the swelling increases with temperature. As a result, the contact area between the fluorinated cation-exchange resin and electrode varies with ambient conditions. It is therefore necessary to control the contact area, in order to control the current density.

The electrolytic cell shown in FIG. 4 has a characteristic structure suitable for surface cleaning or treatment. The cell includes the cathode chamber 41, middle chamber 48 and anode chamber 50, fluorinated cation-exchange membrane 45 provided to separate the cathode chamber 41 and middle chamber 48 from each other, cathode 44 closely attached to the cation-exchange membrane 45 on the side facing the cathode chamber 41, cation exchange resin 46 contained in the middle chamber 48 and arranged to come into contact with the cation-exchange membrane 45 on the opposite side facing the middle chamber 48, cation-exchange membrane 54 provided between the middle chamber 48 and anode chamber 50, wherein the feedwater is passed through the anode chamber 50 and the produced electrolytic water discharged from the anode chamber 50 is recovered as the charged anode water. The other components of the electrolytic cell shown in FIG. 4 are the cathode chamber inlet 42, cathode chamber outlet 43, middle chamber inlet 47, middle chamber outlet 49, anode chamber inlet 51 and anode chamber outlet 52.

Embodiment 2

Figure 5:
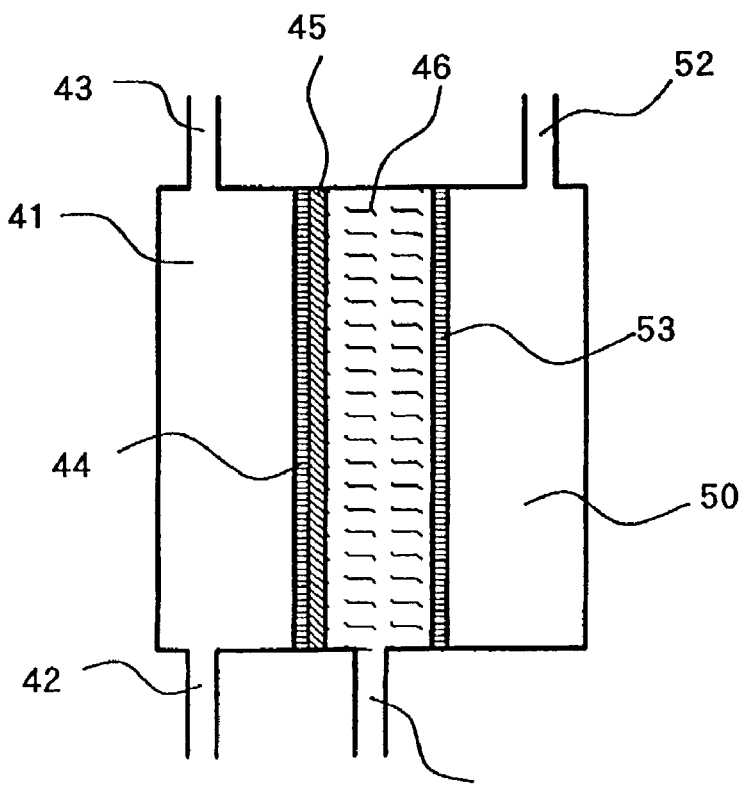
FIG. 5 shows the schematic cross-sectional view of the electrolytic cell in the second embodiment of the present invention.

The electrolytic cell shown in FIG. 5 has a characteristic structure in that the feed water flows into the middle chamber 46 and the electrolyzed water discharged from the anode chamber 50 is recovered as the charged anode water. The cell structure as those shown in FIG. 4 are given the same number and their descriptions is omitted.

Embodiment 3

Figure 6:
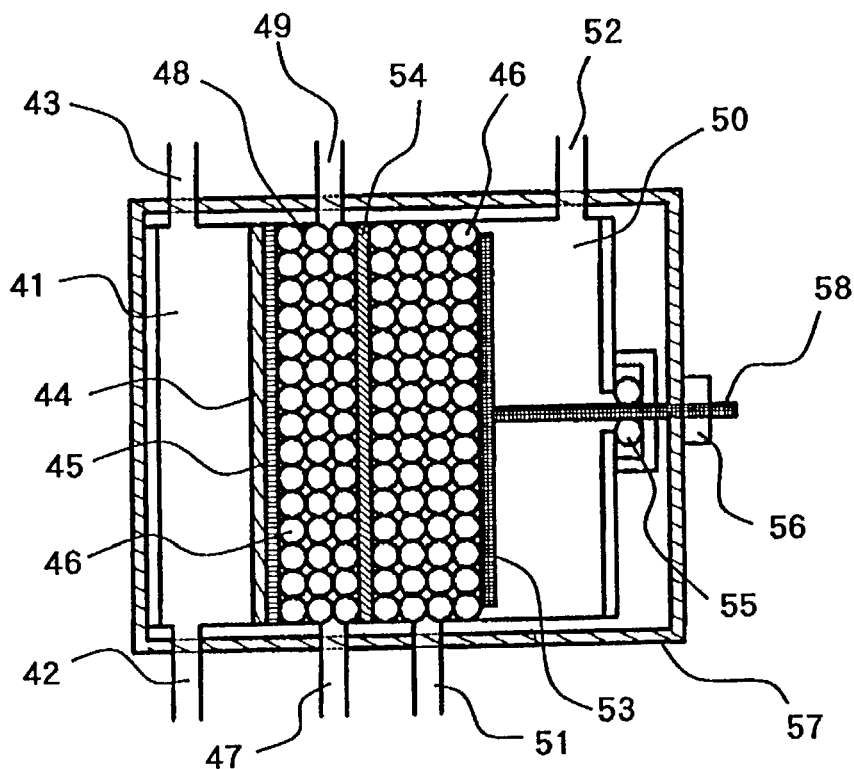
FIG. 6 shows the schematic cross-sectional view of the electrolytic cell in the third embodiment of the present invention.

The electrolytic cell structure includes a mechanism to adjust the position of anode 53 in the current flowing direction, as shown in FIG. 6. This structure is provided with a frame, outside of the cell, which holds the mobile anode position-adjusting mechanism.

The anode position adjusting mechanism typically is composed of an anode-supporting rod provided with a screw, by which the anode position can be adjusted.

The structure is described in more detail. This structure makes it possible to adjust position of the anode 53, shown in FIG. 4 for embodiment 1, in the current passing direction. More specifically, the anode-supporting rod 58 is set at approximately center of the anode 53 in the current passing direction, held by the holding frame 57 provided in the anode chamber 50 in such a way to be movable in the axial direction, and screwed into the position-adjusting mechanism 56, provided outside of cell, via the O-ring 55 which seals the anode-supporting rod 58. The position can be adjusted by cutting the anode-supporting rod 58 to have male threads and the position-adjusting mechanism 56 to have the corresponding female threads. Position of the anode 53 is adjusted by rotating the position-adjusting mechanism 56 to control the effective electrolysis current. This means the increase in the electrolysis voltage. Detaching the anode 53 from the cathode side improves charging characteristics of the cell.

The same components as those describe in embodiment 1 are given the same numbers and their descriptions are omitted.

EXAMPLES

Example 1

The three-chamber type electrolytic cell shown in FIG. 4 was used, where ultra pure water was supplied to the inlets of the anode chamber 50, middle chamber 48 and cathode chamber 41. The ultra pure water had the following properties:
Resistively; 18.0 MΩ/cm
Water temperature: 15° C.
Opening diameter: 4φ

Electrode: Platinum plated titanium electrode was used.
Ion-exchange membrane: The membrane 45 was made of a fluorinated cation-exchange membrane (Nafion 117 made by Du Pont)
Ion exchange resin filled in the middle chamber: The middle chamber 48 was filled with a granular fluorinated cation-exchange resin (Nafion NR50 made by Du Pont).
Ion exchange filled in the anode chamber: the room between the anode 53 and membrane 45 was also filled with NR50.
Water flow rate: ultra pure water was passed at 0.75 l/min. through the cathode chamber 41 and anode chamber 50.
The perforated anode 53 assembled in the electrolytic cell used in the example 1 had an apparent area of 48 cm$^2$.
The apparent area of the electrode (the openings were two-dimensionally evenly arranged in the Example 1 as follows.
Electrode thickness; 1 mm
Total opening area: 16.23 cm$^2$
Opening ratio; 34%

Figure 7:
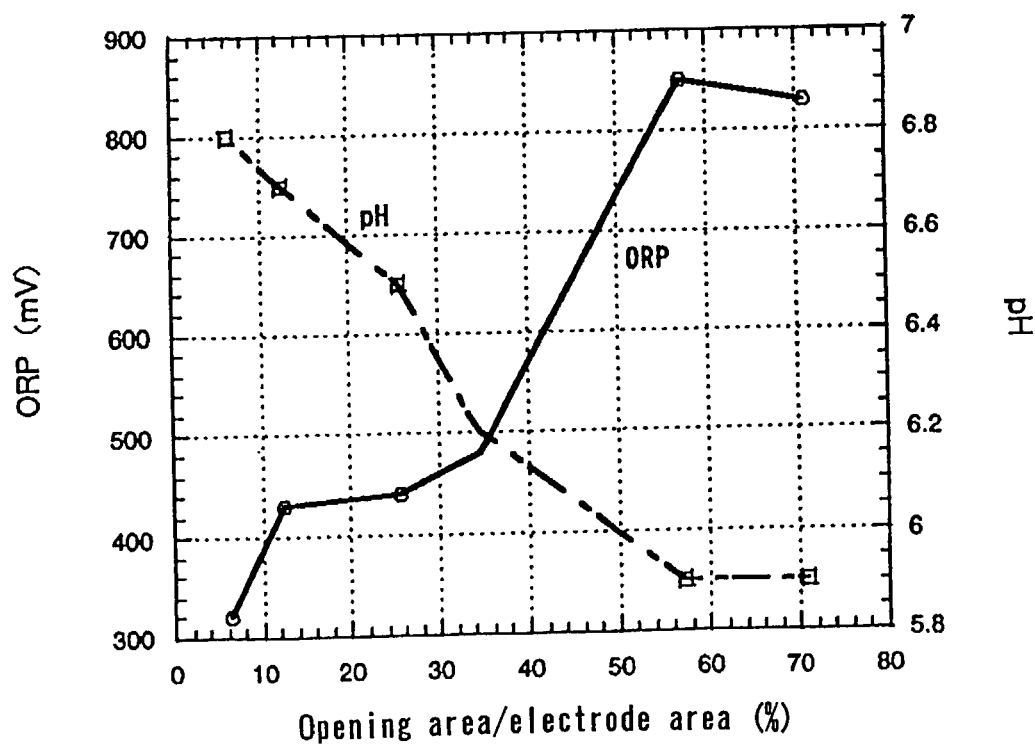
FIG. 7 shows the influence of the area ratio on pH and ORP values of the electrolytic anode water prepared in the example 1.

The ratio of the opening area to the apparent electrode area was changed to obtain the relationship between the ratio and the pH and ORP of charged anode water where the apparent electrolytic current was set at 5 A, as shown in FIG. 7. The electrolysis voltage was very low and around 14 v under this condition. As clear from the figure, measured pH and ORP values, which are characteristic of the anode water, are very sensitive to the area ratio.

Example 2

Figure 8:
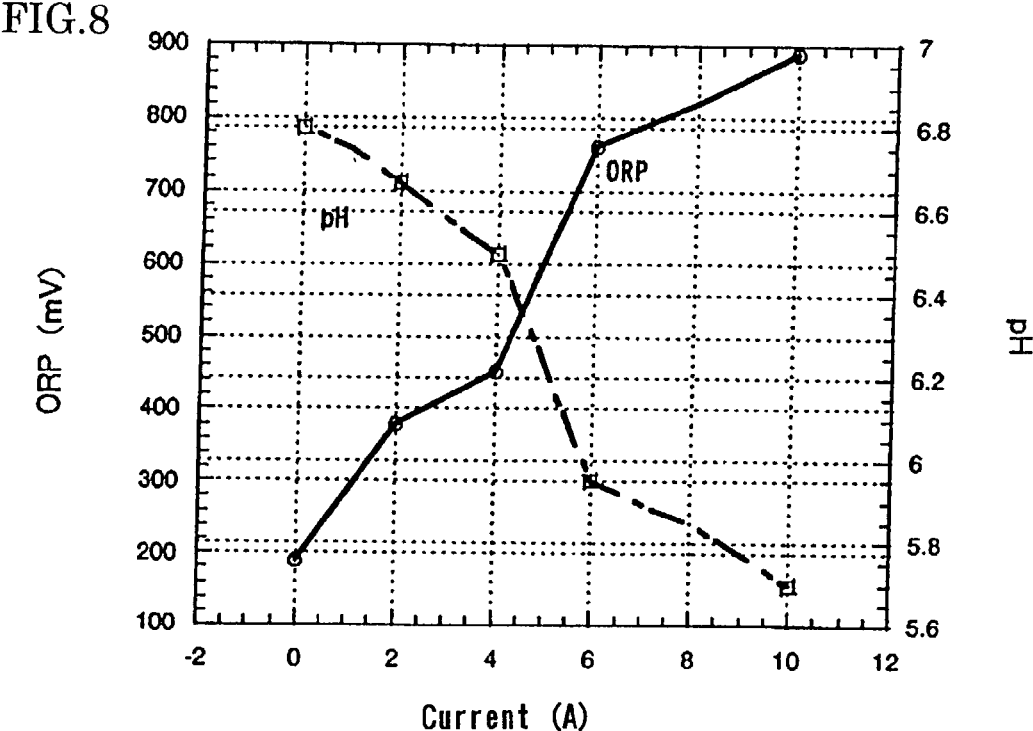
FIG. 8 shows the influence of electrolytic current on pH and ORP values of the electrolytic anode water prepared in the example 2.

The effects of electrolytic current on characteristics of anode water were investigated using the same electrolytic cell and ultra pure water as those use in the example 1. FIG. 8 shows the effects of electrolytic current on pH and ORP of the anode water. The charging characteristics such as pH and ORP were improved as the current density was increased.

Example 3

Figure 9:
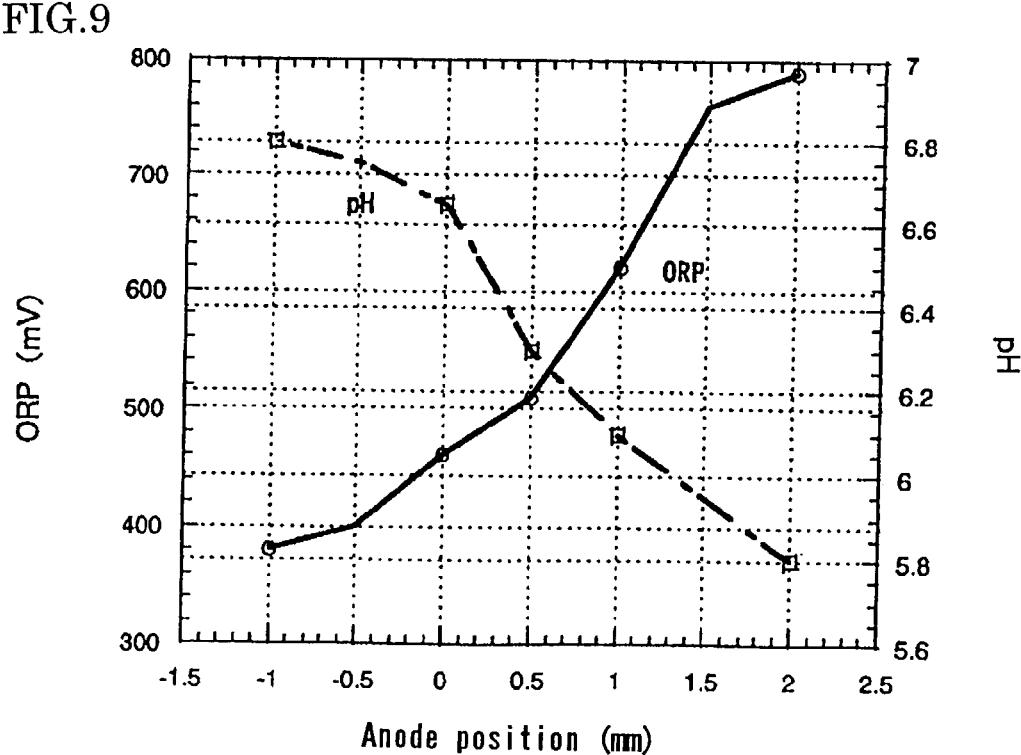
FIG. 9 shows the influence of the anode position on charging characteristics of the anode water prepared in the example 3.

The electrolytic cell with adjusting function of anode position shown in FIG. 6 was used to investigate the relationship between the anode electrode position and the charging characteristics such as pH and ORP of anode water, where apparent electrolytic current was set at 4 A. FIG. 9 indicates the result.

The minus position of anode in FIG. 9 indicates that the anode approached towards the cathode side. In order set the electrolytic current at a given level, the electrolytic voltage was decreased, as the anode position was moved toward the cathode side. As the position of anode was moved toward the counter side, the charging characteristics such as pH and ORP were improved. These results shows that the effective contact area between the cation exchange resins and anode decreases as the anode is move towards the counter side. The fluorinated ion exchange resin used in the example 3 had rubber like elasticity and was capable of reversibly changing the charging characteristics.

Example 4

Figure 10:
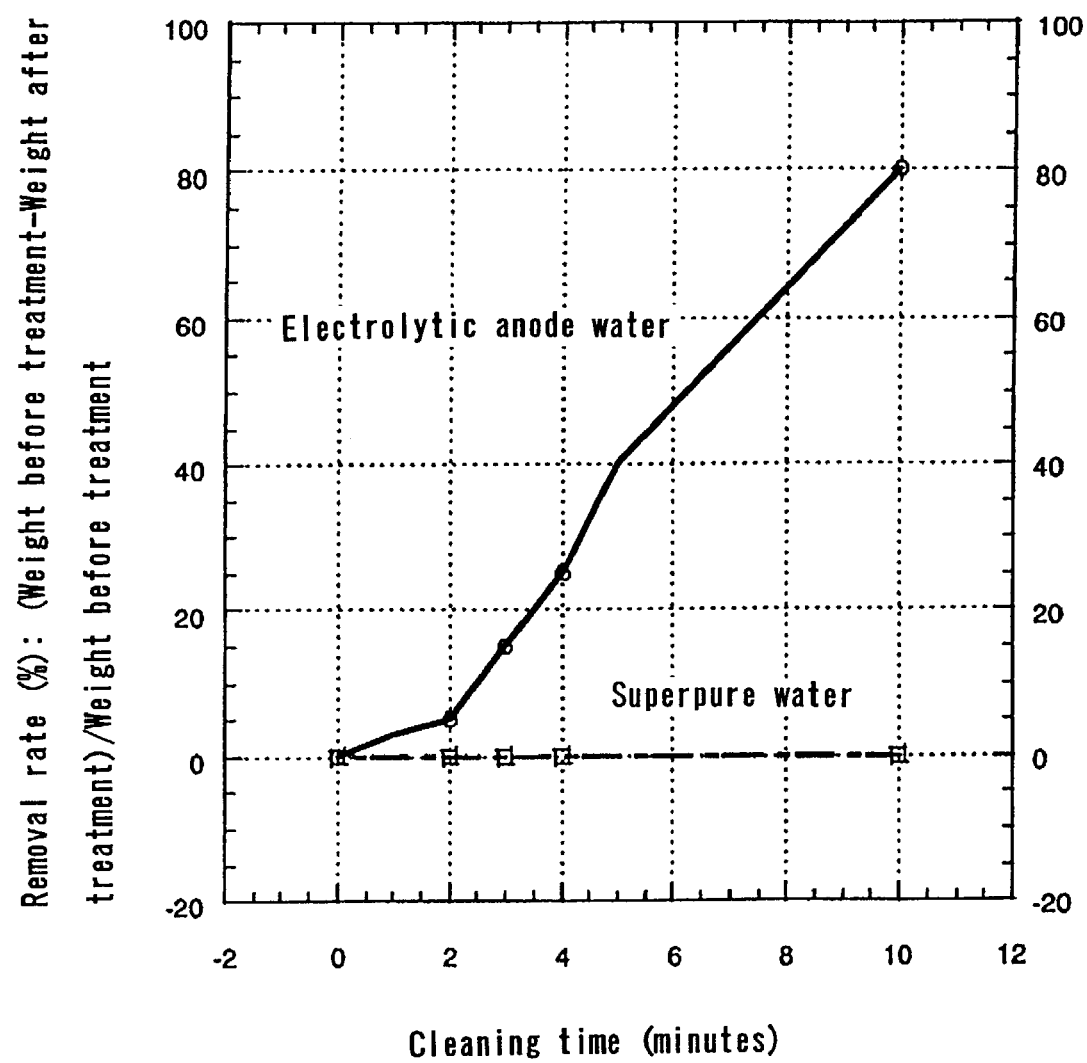
FIG. 10 shows the relationship between removal rate and cleaning time obtained in the example 4.

In this example, the anode water was used to confirm the cleaning efficiency. The object to be cleaned was polyethylene plate on which a printing paint (base material was an acrylic resin) containing carbon black was spread. The electrolytic cell was the same one as that used in the example 1, where ultra pure water was supplied to each chamber at the flow rate of 0.75 l/min, and electrolytic current was set at 7A. The anode water thus produced was run at the same flow rate on the surface of the polyethylene plate for cleaning. FIG. 10 shows the cleaning efficacy, which was defined as the difference between the object weight before and after cleaning divided by the weight before cleaning. For comparison, the ultra pure water without electrolysis was used for cleaning the plate. FIG. 10 indicates that anode solution exhibits a higher cleaning efficacy.

Example 5

Next, the effects of anode water on the removal rate of fine particles on silicon wafer were investigated. First, the 8-inch bare wafer was placed on rubber to contaminate with fine particles thereon. The number of fine particles adhered to the wafer surface was ranging from 2,000 to 4,000. Then, The wafer was washed with the electrolytic anode water, which was produced under the same condition as in the example 1, where the electrolytic current was se at 5 A. The electrolytic water was kept in a PFA bottle (20 l), from which the water was run onto the wafer at the flow rate of 3 l/min using a diaphragm pump. The overall schedule is described as follows.

Cleaning with ultra pure water (2 minutes)→cleaning with electrolytic water (3 minutes)→drying by using s spin drier (2 minutes).

The silicon wafer was also cleaned with ultra pure water in place of the electrolytic water for comparison. Table 1 shows the cleaning results.

TABLE 1

| pH | ORP | removal rate total (%) |
|---|---|---|
| 6.8 | 430 | 31.5 |
| 6.5 | 460 | 46.3 |
| 6.2 | 510 | 60.8 |
| 5.9 | 680 | 89.0 |
| 5.5 | 720 | 99.5 |

Example 6

In this example, glass substrates for hard disks were treated with electrolytic water.

When a hard disk glass was immersed in the anode water, the surface compositions of hard disk glass were found to change. This glass contained cation such as $Na^+$, $K^+$, and $H^+$, bonded in the bonding network of Si—O.

Sodium ions is known to damage the surface and so desired to remove from surface region to prevent surface roughing. In order to confirm the possibility of ion exchanging effects in anode solution, glass was immersed in the anode water and then the depth profile of cation distribution in a surface layer was measured.

Figure 11:
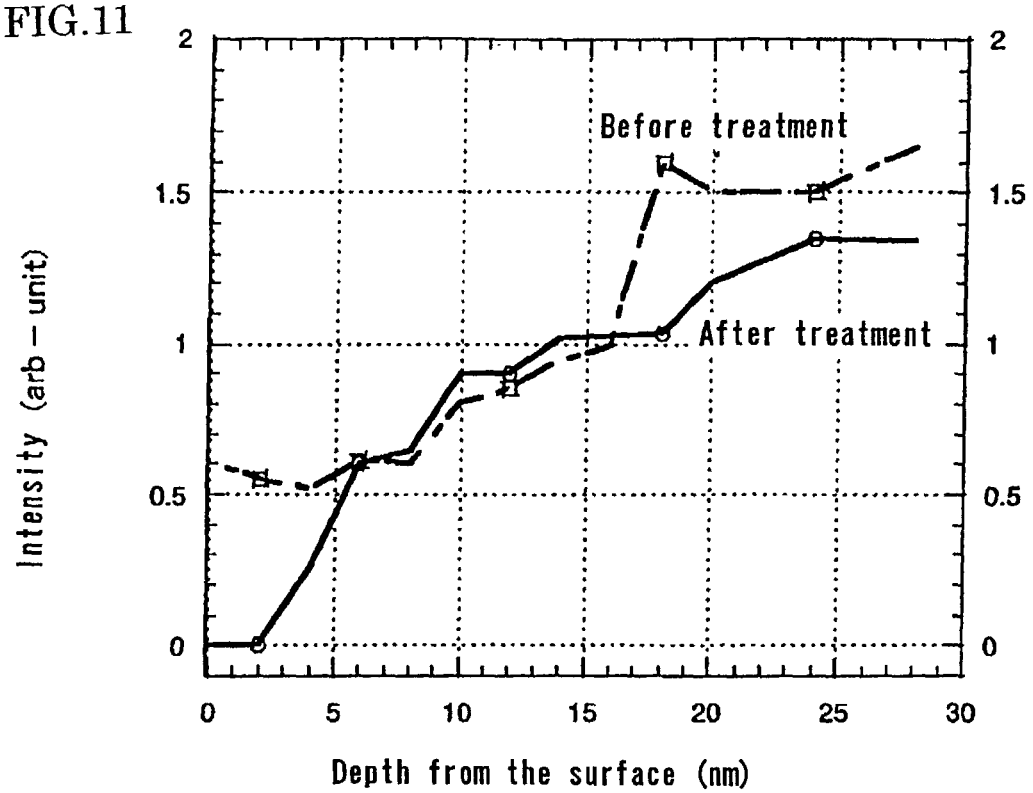
FIG. 11 shows the $Na^+$ ion distribution in the depth direction before and after the treatment, observed in Example 6.

The charged water was produced by using the same electrolytic cell as use in the example 1, where electrolytic current was set at 5 A. The glass was immersed in the charged anode solution for 5 minutes, to observe the surface composition by using an Auger analyzer. FIG. 11 shows the $Na^+$ ion distribution in the depth direction before and after immersion. As shown in FIG. 11, immersing the glass in the anode solution decreases the $Na^+$ ion concentration in the surface layer.

Example 7

Figure 12:
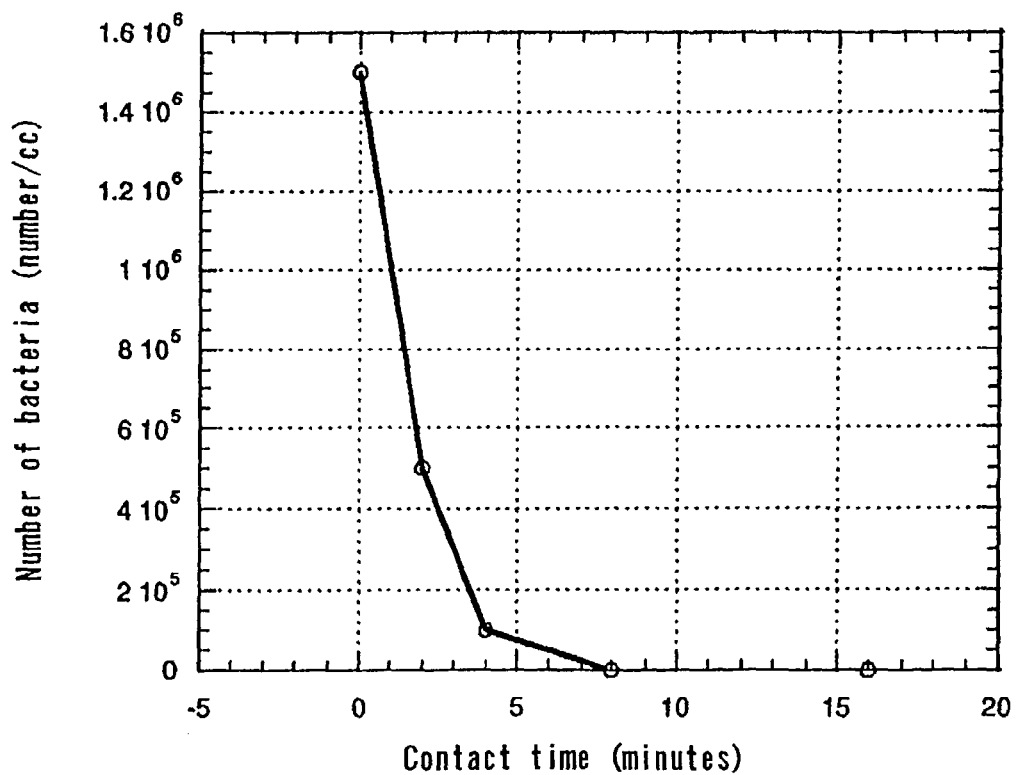
FIG. 12 shows the relationship between the number of bacteria and the contact time with electrolytic anode water prepared in the example 7.
Figure 13:
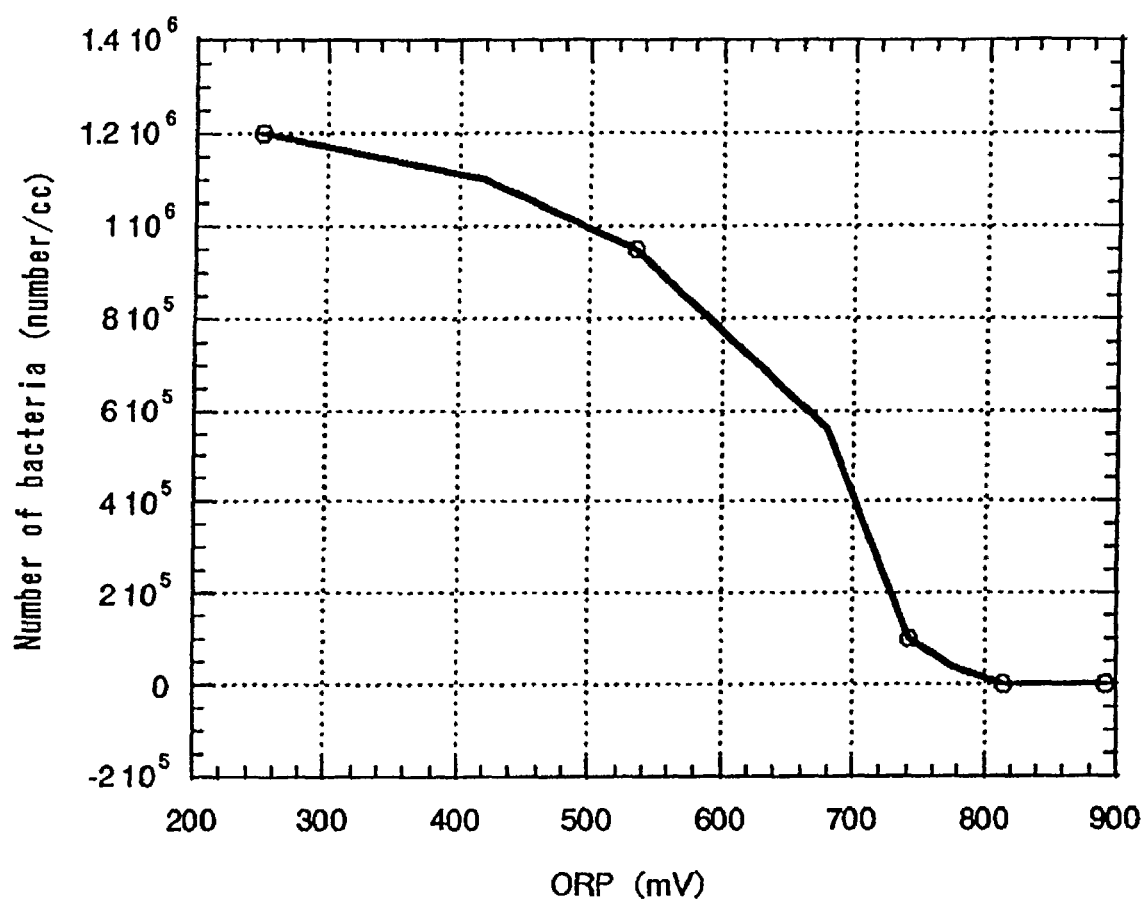
FIG. 13 shows the relationship between the number of bacteria and ORP of the electrolytic anode water prepared in the example 7.

The antimicrobial activities of anode water were investigated using the electrolytic cell of present invention. The anode water was produced by using the same cell as used in the example 1, where electrolytic current was set at 8 A. A bacteria containing solution was prepared, where the number of *Escherichia coli* was adjusted to around 107. One part of the bacteria-containing solution was mixed with 30 parts of the anode solution. The mixture, stirred for a give time, was spread on the standard agar culture medium to culture the bacteria at 30° C. for 24 hours and the number of the bacteria was countered. FIG. 12 shows the relationship between the number of bacteria and the contact time with the anode water. FIG. 13 sows the sterilization effect of the anode water, where the number of bacteria is plotted against ORP of the water. FIGS. 12 and 13 indicates that the anode water exhibits the sterilization effect when the ORP level exceed 800 mV.

Example 8

Figure 14:
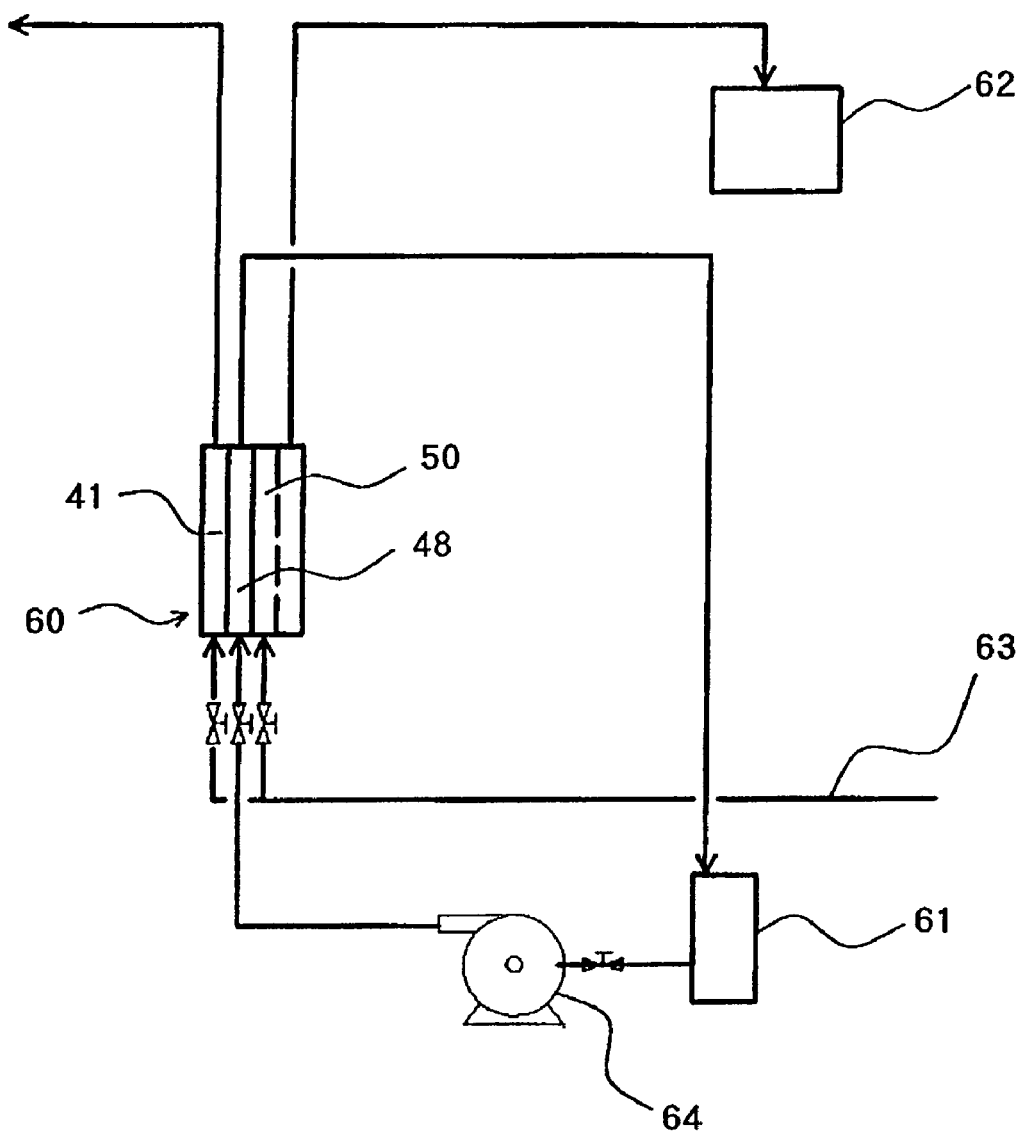
FIG. 14 shows the electrolytic cell system in which a cooler is built.
Figure 15:
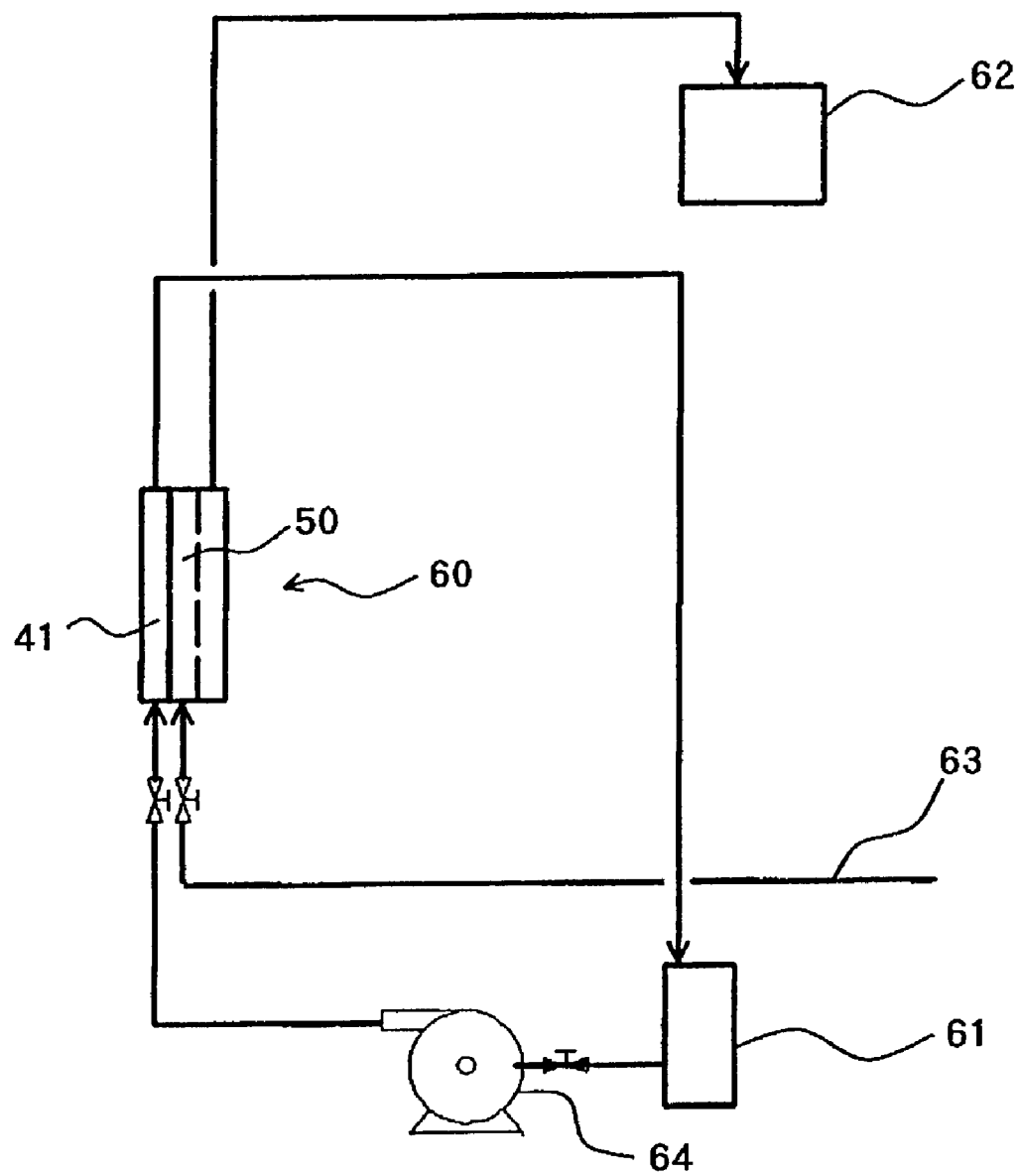
FIG. 15 shows the electrolytic cell system in which a cooler is built.
Figure 16:
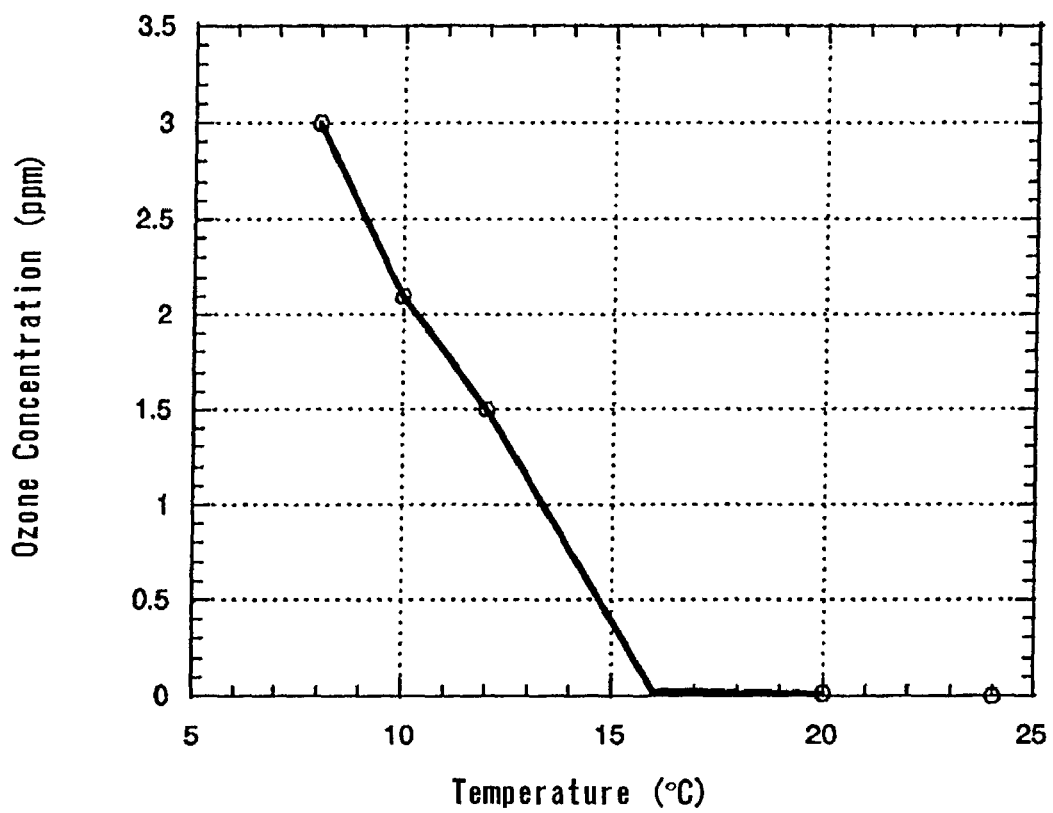
FIG. 16 shows the relationship between the ozone concentration and temperature in the middle chamber obtained in the example 8.

Oxidation capacity of the anode solution produced by an electrolytic cell is also very sensitive to electrolysis temperature. As the temperature decreases, the ozone production efficacy increases and then the oxidation capacity increases. Cooling is a good method for decreasing the temperature in the electrolytic cell. The cooling system depicted in FIG. 14 and 15 can keep temperature of water in a middle chamber or cathode chamber at low level, to improve ozone production efficiency. FIG. 16 shows that the ozone production efficiency changes with temperate in electrolytic cell used in the example 1 with the cooling system shown in FIG. 14. In FIGS. 14 and 15, same components as those described in embodiments are given the same numbers and their descriptions are omitted. The other components are the three-chamber type electrolytic cell 60, cooler 61, anode electrolytic water tank 62, feed water line 63 and pump 64.

Example 9

Figure 17:
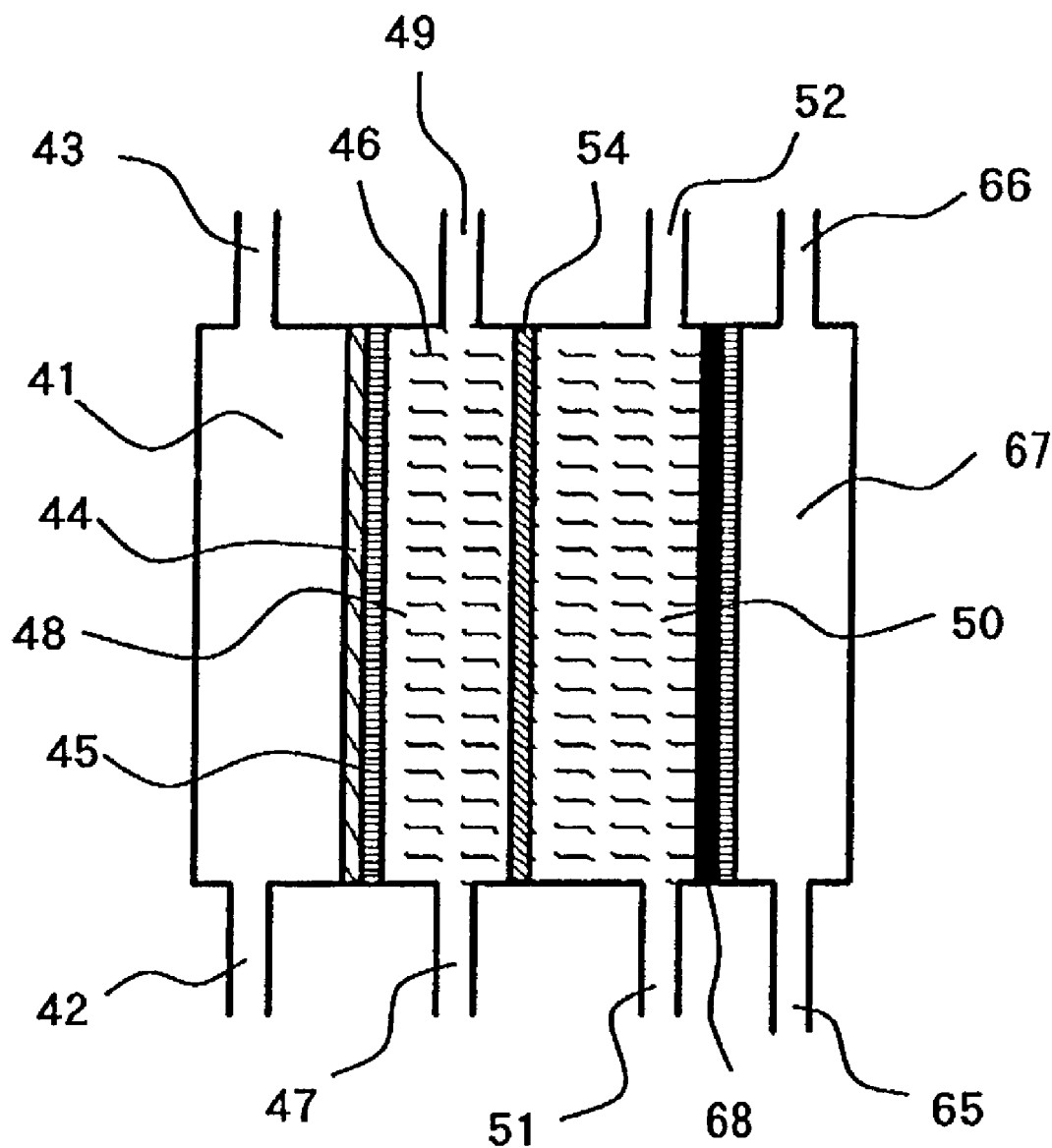
FIG. 17 shows the schematic cross-sectional view of the electrolytic cell in which a cooling chamber is built, described in the example 9.

The example 9 describes another cooling method. As depicted in FIG. 17, the anode chamber is divided into the camber through which the anode water flows and the other chamber through which cooling water flows. In FIG. 17, the same components as those described in the embodiment 1 are given the same numbers and their descriptions are omitted. The other components are the cooling chamber inlet 66, cooling chamber outlet 65, cooling chamber 67 and baffle 68.

Figure 18:
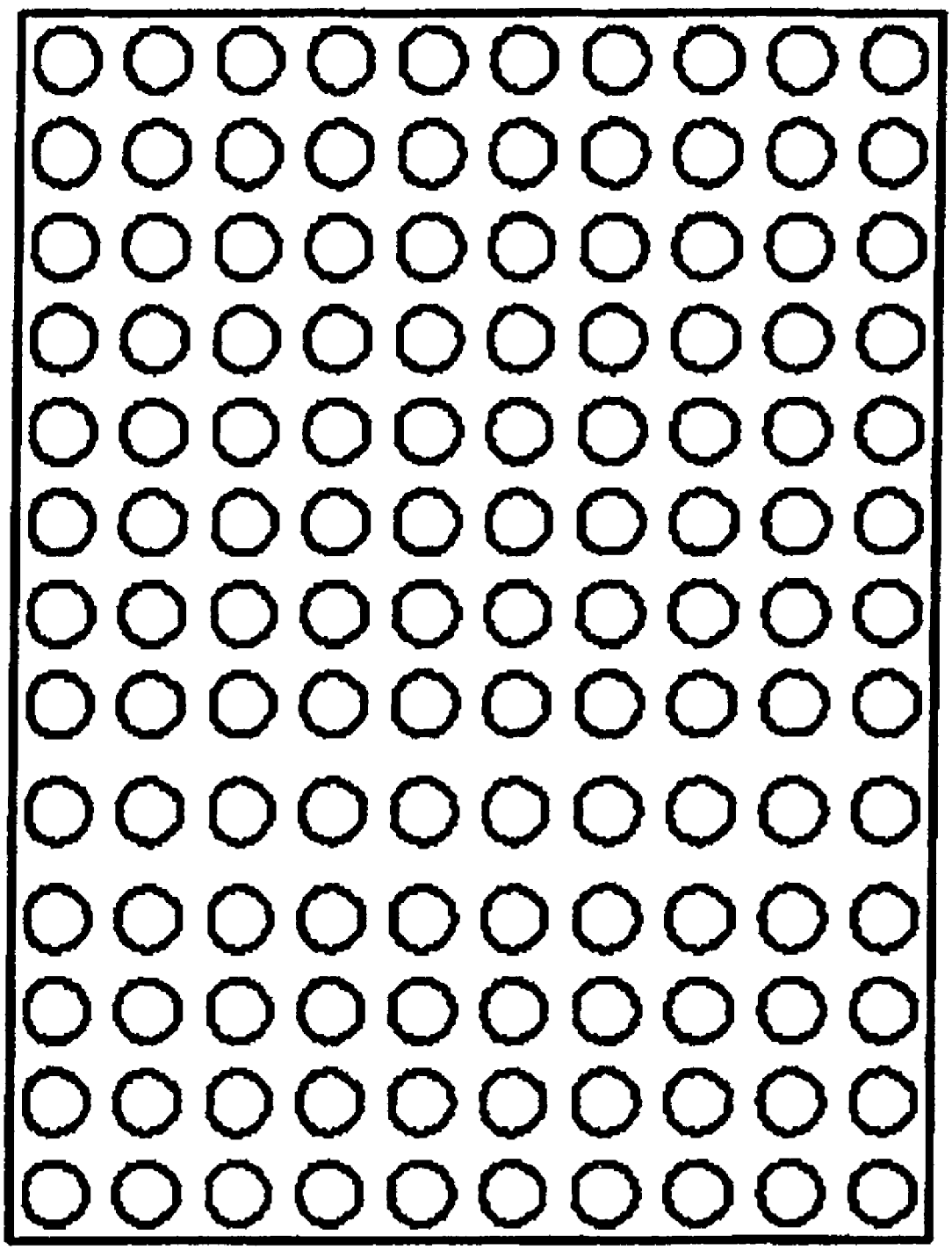
FIG. 18 shows the schematics of a PTFE sheet.

In this case, the anode was not provided with openings. However, a perforated PTFE (fluorocarbon resin) shown in FIG. 18 was placed on a surface of the anode of platinum-plated titanium, 80 by 60 mm, to increase effective current density on the anode. In this example, the PTFE sheet, 60 by 80 mm, was provided with openings of 4 mm in diameter, as shown in FIG. 18.

Figure 19:
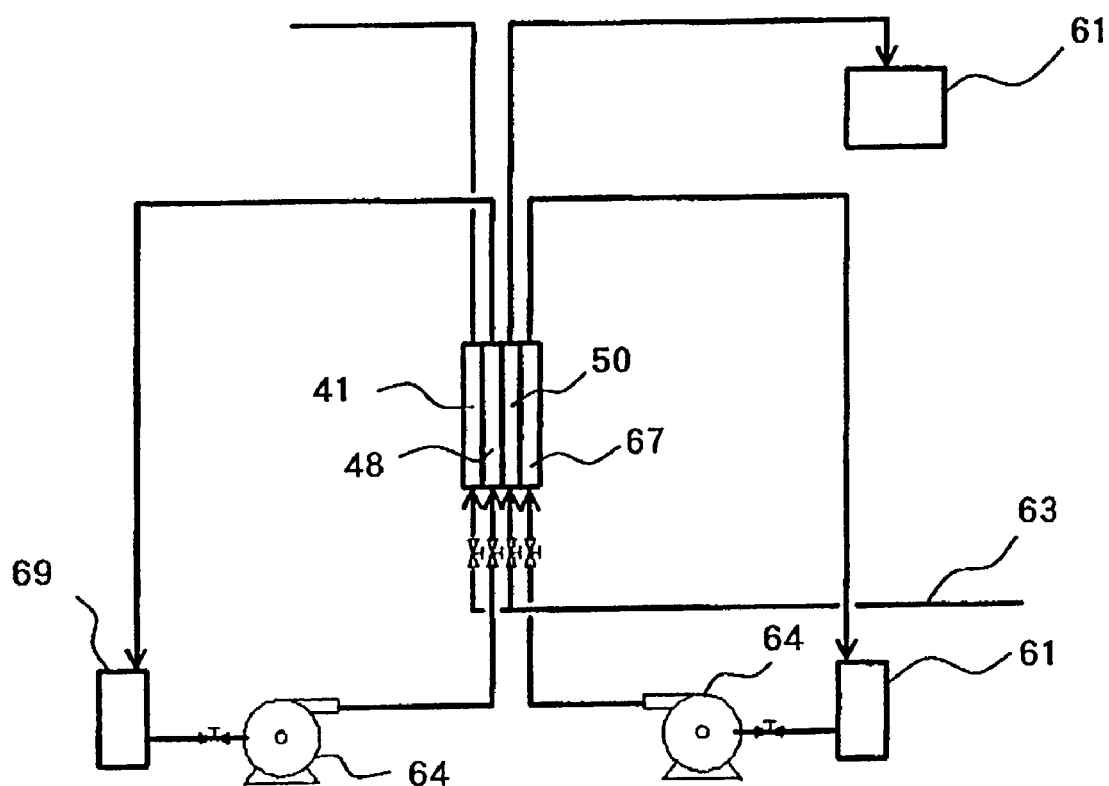
FIG. 19 shows the system diagram of the electrolytic cell in which a cooling chamber is built.

Temperature in the electrolytic cell was controlled by the system shown in FIG. 19, which passed cooling water to cooling chamber to directly cool the anode. In FIG. 19, the same components as those described in the embodiment are omitted. The other components include the liquid tank 69 in the middle chamber. Keeping temperature in the electrolytic cell at a low level by using the cooler improved ozone production efficiency, as described in the example 8.

The electrolytic cell of the present invention can produce strongly charged anode water. Moreover, It can improve ozone production efficiency, when its anode is cooled. The charged water produced by the electrolytic cell is effective for cleaning a silicon wafer by removing fine particles or the like wherefrom or glass surface treatment for promoting ion exchanging on the surface to prevent surface roughing. It is also effective for cleaning resins or the like, in particular resins for medical devices. For Example, it is effective for cleaning and sterilizing the inner surfaces of catheters or like. No special chemical remains after cleaning, which is its advantage.

What is claimed is:

1. An electrolytic cell for producing charged anode water suitable for surface cleaning or treatment, comprising cathode, middle and anode chambers, a fluorinated cation-exchange membrane provided to separate cathode and middle chambers from each other, a cathode closely attached to the cation-exchange membrane on the side facing the cathode chamber, and a middle chamber filled with fluorinated cation-exchange resins, provided on the other side of the cation-exchange membrane, the cation-exchange resins being arranged in such a way to come into contact with the fluorinated cation-exchange membrane in the cathode chamber side and with the anode in the anode chamber side, wherein the feed water is fed into the middle chamber and passed through the fluorinated cation-exchange resins to be recovered as the charged anode water.

2. The electrolytic cell for producing charged anode water suitable for surface cleaning or treatment according to claim 1, wherein a porous anode is provided, and said middle chamber has an inlet but no outlet for the feed water to be treated and said anode chamber has an outlet for the treated water but no inlet for the feed water.

3. The electrolytic cell for producing charged anode water suitable for surface cleaning or treatment according to claim 2, wherein holes in said porous anode have a total area of 10% or more of a whole electrode area.

4. The electrolytic cell for producing charged anode water suitable for surface cleaning or treatment according to claim 2, wherein said electrode has an ineffective area, which has no contribution to electrolysis, of 10% or more of the whole electrode area.

5. The electrolytic cell for producing charged anode water suitable for surface cleaning or treatment according to claim 2, wherein a mechanism of controlling position of said anode in the direction of current passing towards said cation-exchange resins is provided.

6. The electrolytic cell for producing charged anode water suitable for surface cleaning or treatment according to claim 2, wherein said cation-exchange resin is fluorinated.

7. The electrolytic cell for producing charged anode water suitable for surface cleaning or treatment according to claim 1, wherein said electrode has an ineffective area, which has no contribution to electrolysis, of 10% or more of the whole electrode area.

8. The electrolytic cell for producing charged anode water suitable for surface cleaning or treatment according to claim 7, wherein a mechanism of controlling position of said anode in the direction of current passing towards said cation-exchange resins is provided.

9. The electrolytic cell for producing charged anode water suitable for surface cleaning or treatment according to claim 7, wherein said cation-exchange resin is fluorinated.

10. The electrolytic cell for producing charged anode water suitable for surface cleaning or treatment according to claim 1, wherein a mechanism of controlling position of said anode in the direction of current passing towards said cation-exchange resins is provided.

11. The electrolytic cell for producing charged anode water suitable for surface cleaning or treatment according to claim 10, wherein said cation-exchange resin is fluorinated.

12. The electrolytic cell for producing charged anode water suitable for surface cleaning or treatment according to claim 1, wherein said cation-exchange resin is fluorinated.

13. An electrolytic cell for producing charged anode water suitable for surface cleaning or treatment, comprising cathode, middle and anode chambers, a first fluorinated cation-exchange membrane provided to separate the cathode and middle chambers from each other, a cathode closely attached to the cation-exchange membrane on the side facing the cathode chamber, cation exchange resins contained in the middle chamber and arranged to come into contact with the cation-exchange membrane on the opposite side facing the middle chamber, a second fluorinated cation-exchange membrane provided between the middle and anode chambers, fluorinated cation-exchange resins contained in the space between the second fluorinated cation-exchange membrane and the anode, wherein the feed water is passed over the anode surface and electrolytic water discharged from the anode chamber is recovered as the charged anode water.

14. The electrolytic cell for producing charged anode water suitable for surface cleaning or treatment according to claim 13, wherein a fluorinated cation-exchange membrane is arranged in said middle chamber to divide the chamber into a first middle chamber on the cathode chamber side and a second middle chamber on the anode chamber side.

15. The electrolytic cell for producing charged anode water suitable for surface cleaning or treatment according to claim 14, wherein said electrode has an ineffective area, which has no contribution to electrolysis, of 10% or more of the whole electrode area.

16. The electrolytic cell for producing charged anode water suitable for surface cleaning or treatment according to claim 14, wherein a mechanism of controlling position of said anode in the direction of current passing towards said cation-exchange resins is provided.

17. The electrolytic cell for producing charged anode water suitable for surface cleaning or treatment according to claim 14, wherein said cation-exchange resin is fluorinated.

18. The electrolytic cell for producing charged anode water suitable for surface cleaning or treatment according to claim 13, wherein said electrode has an ineffective area, which has no contribution to electrolysis, of 10% or more of the whole electrode area.

19. The electrolytic cell for producing charged anode water suitable for surface cleaning or treatment according to claim 13, wherein a mechanism of controlling position of said anode in the direction of current passing towards said cation-exchange resins is provided.

20. The electrolytic cell for producing charged anode water suitable for surface cleaning or treatment according to claim 13, wherein said cation-exchange resin is fluorinated.

* * * * *